United States Patent
Kandadai et al.

(10) Patent No.: US 12,415,070 B2
(45) Date of Patent: Sep. 16, 2025

(54) BENEFIT AGENT DELIVERY SYSTEM COMPRISING REVERSE MICELLES

(71) Applicant: E INK CORPORATION, Billerica, MA (US)

(72) Inventors: Madhuvanthi Agaram Kandadai, Fremont, CA (US); HongMei Zang, Fremont, CA (US)

(73) Assignee: E Ink Corporation, Billerica, MA (US)

( * ) Notice: Subject to any disclaimer, the term of this patent is extended or adjusted under 35 U.S.C. 154(b) by 750 days.

(21) Appl. No.: 17/852,603

(22) Filed: Jun. 29, 2022

(65) Prior Publication Data

US 2023/0001188 A1    Jan. 5, 2023

Related U.S. Application Data

(60) Provisional application No. 63/216,818, filed on Jun. 30, 2021.

(51) Int. Cl.
| | | |
|---|---|---|
| *A61N 1/04* | (2006.01) | |
| *A61L 9/04* | (2006.01) | |
| *A61L 9/12* | (2006.01) | |
| *A61N 1/32* | (2006.01) | |
| *C11B 9/00* | (2006.01) | |

(52) U.S. Cl.
CPC ............. *A61N 1/325* (2013.01); *A61L 9/044* (2013.01); *A61L 9/12* (2013.01); *C11B 9/00* (2013.01)

(58) Field of Classification Search
CPC .... A61K 9/0009; A61K 9/703; A61K 9/7084; A61K 9/7092; C25F 5/00; A61M 37/00; A61M 2037/0007; A61M 2205/0216; A61M 2205/0233; A61M 2205/0238; A61M 2207/10; A61M 35/10; A61M 35/00; A61M 2205/055; A61N 1/0428
See application file for complete search history.

(56) References Cited

U.S. PATENT DOCUMENTS

| | | |
|---|---|---|
| 5,582,700 A | 12/1996 | Bryning et al. |
| 6,564,093 B1 | 5/2003 | Tannenbaum |
| 6,933,098 B2 | 8/2005 | Chan-Park et al. |
| 7,715,088 B2 | 5/2010 | Liang et al. |
| 10,087,344 B2 | 10/2018 | Moran |

(Continued)

FOREIGN PATENT DOCUMENTS

CN    108314702 A    7/2018

OTHER PUBLICATIONS

Liu, Yan et al., "Lecithin/isopropyl myristate reverse micelles as transdermal insulin carriers: Experimental evaluation and molecular dynamics simulation", Journal of Drug Delivery Science and Technology, vol. 59, Oct. 2020.

(Continued)

*Primary Examiner* — Deanna K Hall
(74) *Attorney, Agent, or Firm* — Ioannis Constantinides

(57) ABSTRACT

A benefit agent delivery system can deliver benefit agents on demand. The benefit agent delivery system comprises a first electrode layer, a microcell layer comprising a plurality of microcells, and a porous second electrode layer. Each microcell of the plurality of microcells are filled with a liquid mixture comprising reverse micelles in a hydrophobic liquid that are formed from a polar liquid, an ionic surfactant, and a benefit agent. Application of an electric field on the microcell layer affects the rate of release of the benefit agent through the porous second electrode layer.

20 Claims, 13 Drawing Sheets

(56) References Cited

U.S. PATENT DOCUMENTS

| | | |
|---|---|---|
| 11,543,725 B2 | 1/2023 | Zang |
| 2003/0027339 A1 | 2/2003 | Monahan et al. |
| 2003/0113366 A1 | 6/2003 | Macgregor |
| 2015/0301425 A1 | 10/2015 | Du et al. |
| 2018/0272114 A1 | 9/2018 | Liu et al. |
| 2019/0143105 A1 | 5/2019 | Liu |
| 2021/0154133 A1 | 5/2021 | Liu |

OTHER PUBLICATIONS

European Patent Office, "The Extended European Search Report", EP Appl. No. 22834072.5, Mar. 31, 2025.
European Patent Office, "The Extended European Search Report", EP Appl. No. 22834119.4, Apr. 14, 2025.
Korean Intellectual Property Office, "International Search Report and Written Opinion", PCT/US2022/035332, Oct. 24, 2022. Oct. 24, 2022.
Korean Intellectual Property Office, "International Search Report and Written Opinion", PCT/US2022/035453, Oct. 24, 2022. Oct. 24, 2022.
Harvey, T.G.; "Replication techniques for micro-optics"; SPIE Proc. vol. 3099, pp. 76-82; 1997. Jan. 1, 1997.

BENEFIT AGENT DELIVERY SYSTEM COMPRISING REVERSE MICELLES

RELATED APPLICATIONS

This application claims priority to U.S. Provisional Patent Application No. 63/216,818, filed on Jun. 30, 2021, which is incorporated by reference in its entirety, along with all other patents and patent applications disclosed herein.

BACKGROUND OF THE INVENTION

The development of methodologies for controlled and extended release of benefit agents have attracted significant attention during the last decades. This is true for a large variety of benefit agents including pharmaceutical, nutraceutical agents, agricultural nutrients and related substances, cosmetic agents, fragrances, air care agents, and many other benefit agents in a variety of fields. Transdermal delivery of pharmaceutical agents has proven effective for drugs that are able to move across the skin barrier. For example, small amounts of nicotine can be delivered over extended periods with transdermal patches that suspend the nicotine in an ethylene vinyl acetate (EVA) copolymer (see, e.g., Nicoderm-CQ® by GlaxoSmithKline, Brentford, UK). Other examples include extended release of fragrances and malodor removing agents for improving the air quality in living spaces and automobiles, fertilizers in the soil for more efficient food production, and biocides on surfaces for mitigating microorganism growth. Controlled and extended release delivery systems may involve the delivery of various benefit agents in different forms, such as solid, liquid and gas, to different locations, and under different conditions.

A variety of delivery systems has been developed during the last decades that provide on demand delivery of benefit agents. For instance, Chrono Therapeutics (Hayward, CA) has tested a micro pump-enabled smart transdermal patch for delivering nicotine. Nonetheless, the corresponding device is large and visible through clothing as a sizable bump. Thus, there remains a need for small, simple, inexpensive, versatile and safe delivery systems for delivering benefit agents on demand.

SUMMARY OF THE INVENTION

The invention addresses this need by providing a low power delivery system whereby a benefit agent or a mixture of benefit agents can be released on demand. Additionally, as described below, the invention provides a system for delivering varying amounts of benefit agents from the same delivery system at different times, and for delivering multiple benefit agents at the same or different times from the same benefit agent delivery system.

In one aspect, the invention is a benefit agent delivery system comprising a first electrode layer, a microcell layer comprising a plurality of microcells, and a porous second electrode layer. Each microcell has a first opening. The porous second electrode layer spans the first openings of each microcell of the plurality of microcells. The first electrode layer, the microcell layer, and the porous second electrode layer are vertically stacked upon each other. Each microcell contains a liquid mixture comprising reverse micelles in a hydrophobic liquid that are formed from a polar liquid, a surfactant and a benefit agent. The surfactant is an anionic surfactant or a cationic surfactant. The reverse micelles in the hydrophobic liquid may have an average diameter of from 10 nm to 10 μm. Application of a first voltage on a microcell via the first electrode layer and the porous second electrode layer having polarity, which causes the migration of the reverse micelles in the microcell towards the porous second electrode, increases the rate of release of the benefit agent through the porous second electrode layer compared to the rate of release of the benefit agent through the porous second electrode layer when no voltage is applied. Application of a second voltage across a microcell via the first electrode layer and the porous second electrode layer, the second voltage having polarity opposite to the polarity of the first voltage, causes the migration of the reverse micelles in the microcell away from the porous second electrode layer and reduces the rate of release of the benefit agent through the porous second electrode layer compared to the rate of release of the benefit agent through the porous second electrode layer when no voltage is applied. The benefit agent delivery system may further comprise a sealing layer disposed between the microcell layer and the porous second electrode layer. The benefit agent delivery system may comprise a voltage source that is coupled to the first electrode layer and the porous second electrode layer. The reverse micelles of the liquid mixture may further comprise stabilizing particles, in addition to the anionic or cationic surfactant.

In yet another aspect, the invention is a method for operating a benefit agent delivery system. The method for operating the benefit agent delivery system comprises the steps of: (i) providing a benefit agent delivery system comprising (a) a first electrode layer, (b) a microcell layer comprising a plurality of microcells, wherein each microcell includes an opening, and wherein each microcell contains a liquid mixture, wherein the liquid mixture comprises reverse micelles in a hydrophobic liquid that are formed from a polar liquid, an anionic or cationic surfactant, and a benefit agent, (d) a porous second electrode layer spanning the opening of each microcell, and (e) a voltage source that is coupled to the first electrode layer and the porous second electrode layer; wherein the first electrode layer, the microcell layer, and the porous second electrode layer are vertically stacked upon each other; (ii) applying a first voltage on a microcell via the voltage source that causes the migration of the reverse micelles of the microcell towards the porous second electrode, increasing the rate of release of the benefit agent through the porous second electrode layer compared to the rate of release of the benefit agent through the porous second electrode layer when no voltage is applied, and (f) applying a second voltage on a microcell via the voltage source, the second voltage having polarity opposite to the polarity of the first voltage, causes the migration of the reverse micelles of the microcell away from the porous second electrode, reducing the rate of release of the benefit agent through the porous second electrode layer compared to the rate of release of the benefit agent through the porous second electrode layer when no voltage is applied.

BRIEF DESCRIPTION OF THE DRAWINGS

In FIGS. 6C and 6D a combination of top and bottom exposure is used, allowing the walls in one lateral direction to be cured by top photomask exposure, and the walls in another lateral direction to be cured bottom exposure through the opaque base conductor film.

DETAILED DESCRIPTION

Figure 1A:
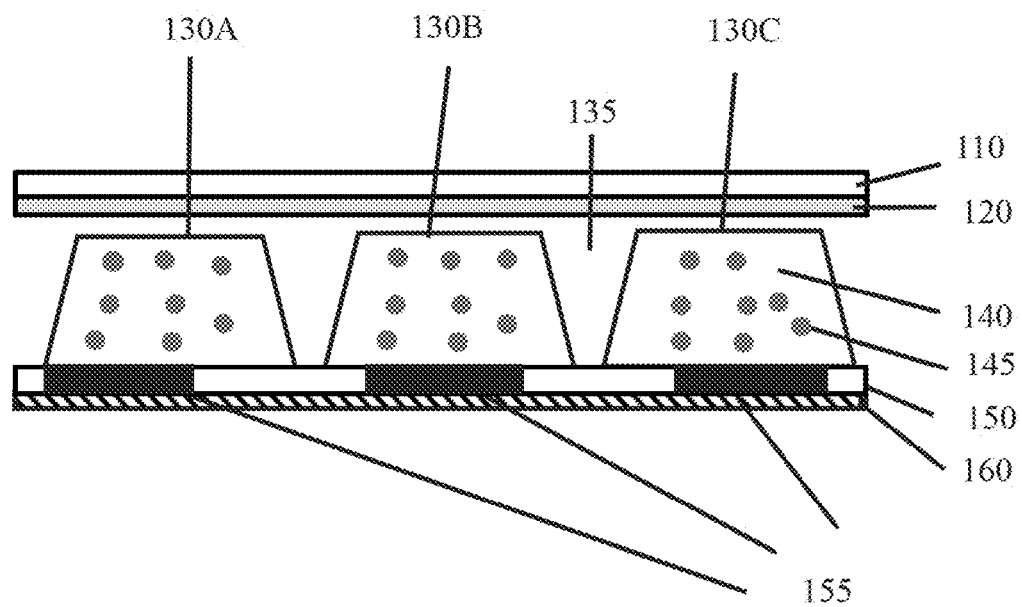
FIG. 1A illustrates an example of a benefit agent delivery system comprising a first electrode layer, a plurality of microcells, each microcell containing reverse micelles in a hydrophobic liquid, and a porous second electrode layer that spans the first opening of each microcell.

The invention provides a benefit agent delivery system whereby benefit agents can be released on demand. A variety of different benefit agents can be delivered from the same system. Different concentrations of benefit agents can also be delivered from the same system. The invention can be used to deliver a pharmaceutical agent, a vaccine, an antibody, a hormone, a protein, a nucleic acid, a nutrient, a nutraceutical agent, a cosmetic agent, a fragrance, a malodor removing agent, an air care agent, an agricultural agent, an air care agent, an anti-microbial agent, a preservative, and other benefit agents. Pharmaceutical agents and cosmetic agents may be delivered to patients transdermally. However, the invention may be used to deliver benefit agents to animals, generally. For example, the invention can deliver tranquilizing agents to a horse during transport. In addition, the invention may be used to deliver benefit agents to other surfaces or spaces.

"Electrocoalescence" is the phenomenon of the increase of the average diameter of an internal phase droplets of an emulsion upon application of an electric field on the emulsion. The emulsion may comprise reverse micelles in a hydrophobic liquid. The term electrocoalescence includes the complete collapse of the reverse micelles into two different layers of liquid phases, a hydrophobic continuous phase layer and a polar liquid phase layer, upon application of an electric field on the reverse micelles in the hydrophobic liquid.

As used herein, the term "two liquid layers" of the liquid mixture means that the liquid mixture comprises two liquid phases (hydrophobic liquid and polar liquid), which form two separate liquid layers. The liquid layers are arranged so that one liquid layer is above the other liquid layer. The liquid layer having higher specific gravity is located at the bottom of the liquid layer having lower specific gravity. Typically, aqueous layers have higher specific gravity and are located below the hydrophobic liquid layer.

"Porous electrode layer" is an electrode layer of the benefit agent delivery system that has average pore size larger than 100 nm. The porous electrode layer also serves as electrode for applying an electric field on the microcell layer. The electric field is applied on the microcell layer via two electrode layers (first electrode layer and porous second electrode layer) that sandwich the microcell layer. The second electrode layer is porous. The first electrode layer or the porous second electrode layer may comprise a plurality of electrodes, which can be independently addressed.

"Porous diffusion layer" is a layer of the benefit agent delivery system that has average pore size that is larger than 0.2 nm. "Rate control layer" is a layer of the benefit agent delivery system that has average pore size that is 0.2 nm or smaller.

"Emulsion" is a material that comprises droplets of liquid A dispersed in liquid B. Liquid A is immiscible to liquid B. Liquid A is part of the internal phase (which can be also called discontinuous phase) of the emulsion. Liquid B is called continuous phase (or external phase) of the emulsion. Typically, the emulsion is stabilized by surfactants or by stabilizing particles. Examples of emulsions include oil-in-water emulsions, where the internal phase is hydrophobic and the continuous phase is aqueous, and water-in-oil emulsions, where the internal phase is aqueous and the continuous phase is hydrophobic. Emulsions stabilized by stabilizing particles are also called "Pickering emulsions". In the case of Pickering emulsions, the stabilizing particles are present in the interface of the internal phase and the continuous phase of the emulsion droplets.

"Reverse micelles" or "reverse micelles in the hydrophobic liquid" are structures that comprise the internal phase of an emulsion, wherein the emulsion comprises droplets of a polar liquid in a hydrophobic liquid. Typically, reverse micelles are stabilized by surfactants or stabilizing particles. The polar liquid may comprise water, a combination of water and a polar organic liquid. The polar liquid may also be anhydrous, comprising a polar organic liquid. In the case of the polar liquid comprising water, the term "reverse micelle" may be also called "water-in-oil emulsion". The polar liquid is typically immiscible with the hydrophobic liquid.

"Hydrophobic liquid" is a liquid that is immiscible with water. It can comprise only one compound or a mixture of compounds. The components of the hydrophobic liquid may have a high clogP value. ClogP of a compound is the logarithm of the partition coefficient between n-octanol and water, that is clog $P=(C_{octanol}/C_{water})$.

"Aqueous liquid" is a liquid that comprises water or water and a water-miscible liquid.

"Surfactant" or "surface active agent" is a substance that can lower the surface tension of a liquid, and the interfacial tension between two liquids, or the interfacial tension between a gas and a liquid, or between a liquid and a solid. Surfactants are usually organic compounds that are amphiphilic, which means that they contain both one or more hydrophobic functional groups (tail) and one or more hydrophilic groups (head). Herein, polymeric material, such as Solsperse and other related polymers, which contain both one or more hydrophobic functional groups and one or more hydrophilic functional groups, are also considered surfactants. "Ionic surfactant" is an anionic or a cationic surfactant; that is, an ionic surfactant has anionic or cationic functional groups in its head.

As used herein, the term "average diameter" of reverse micelles refers to the number mean diameter of reverse micelles in the hydrophobic liquid. The number mean diameter of reverse micelles in a sample may be measured by a light diffraction of measurement apparatus.

As used herein, the term "rate of release", or "release rate", of the benefit agent means the weight of the benefit agent that exits the porous second electrode layer per surface area of sum of the activated microcells per unit of time. The increase in rate of released caused by the application of the electric field compared to the rate of release before the application of the electric field is calculated from the equation: 100×(Rate of release after the application of electric field–Rate of release before the application of electric field)/Rate of release before the application of electric field.

As used herein, the term "direct electric field" or "DC electric field" means that the electric current in the circuit, which provides the electric field via the first electrode layer and the porous second electrode layer, flows in one direction only. On the contrary, as used herein, the term "alternating electric field" or "AC electric field" means that the electric current in the circuit, which provides the electric field via the first electrode layer and the porous second electrode layer, changes direction periodically.

The term "transdermal delivery", as used herein, means the delivery of a benefit agent into the body of a patient through the skin by contacting the intact skin with a benefit agent formulation. Typically, in such delivery, a benefit agent (i.e. a pharmaceutical material) initially penetrates through the stratum corneum and then passes through the deeper epidermis and dermis. When the benefit agent reaches the dermal layer, it becomes available for absorption via the dermal microcirculation.

The term "molecular weight" or "MW" as used herein for polymeric materials refers to the number average molecular weight, unless otherwise stated. The number average molecular weight may be measured by gel permeation chromatography.

"Adhesive layer" of the benefit agent delivery system is a layer that establishes an adhesive connection between two other layers of the system. An adhesive layer may have thickness of from 200 nm to 5 mm, or from 1 μm to 100 μm.

Unless otherwise stated, all percentages of ingredients in compositions disclosed herein refer to weight of the ingredients by total weight of the composition. All such weights as they pertain to ingredients are based on the active level; therefore, they do not include carriers or by-products that may be included in commercially available materials.

In one embodiment of the present invention, the benefit agent delivery system includes a first electrode layer, a microcell layer, and a porous second electrode layer. The first electrode layer, the microcell layer, and the porous second electrode layer are vertically stacked upon each other. In an embodiment, the first electrode layer, the microcell layer, and the porous second electrode layer are vertically stacked upon each other in this order. The benefit agent delivery system may further comprise a sealing layer disposed between the microcell layer and the porous second electrode layer. The benefit agent delivery system may also comprise a voltage source connecting the first electrode layer with the porous second electrode layer.

The microcell layer comprises a plurality of microcells, wherein each microcell contains a liquid mixture. Each of the plurality of microcells may have a volume greater than 0.01 nL, greater than 0.05 nL, greater than 0.1 nL, greater than 1 nL, greater than 10 nL, or greater than 100 nL. The plurality of microcells may have different volumes. That is, not all microcells need to have the same volume.

The microcells of the microcell layer of the benefit agent delivery system of the present invention include an opening. The largest dimension of the microcell opening may be from 30 μm to 300 μm, or from 30 μm to 180 μm, or from about 80 μm to 150 μm. The microcells of the microcell layer of the benefit agent delivery system of the present invention may include two openings at opposite sides of the microcell.

The porous second electrode layer may be a mesh from a metallic material having rows and columns. The porous second electrode layer may also comprise a plurality of electrodes, which may be independently addressed. The average largest dimension of the plurality of electrodes of the porous second electrode layer may be from about 4 μm to about 4 mm, preferably from about 5 μm to about 200 μm, more preferably from about 50 to about 200 µm. The average pore size of the porous second electrode layer may be larger than 0.2 nm, or larger than 10 nm, or larger than 100 nm, or larger than 1 µm, or larger than 10 µm, or larger than 100 µm. The average pore size of the porous second electrode layer may be from 100 nm to 100 µm, or from 500 nm to 10 µm, or from 1 µm to 20 µm. The porous second electrode layer may also have average pore size less than 0.2 nm, In general, the smaller the average pore size, the lower the rate of delivery of the benefit agent from the delivery system. The porosity of the porous second electrode layer may be from about 0.1% to about 80%, or from about 1% to about 60%, or from about 5% to about 40% determined as total volume of pores per total volume of the corresponding sealing layer.

The benefit agent delivery system may comprise a sealing layer disposed between the microcell layer and the porous second electrode layer. The sealing layer may span the first opening of each microcell. The sealing layer comprises a polymeric material. The sealing layer may be constructed from a variety of natural or non-natural polymers, such as comprises acrylates, methacrylates, polycarbonates, polyvinyl alcohols, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polystyrene, polyurethane or alginate. The sealing layer may also comprise a conductive material, such as conductive polymers or conductive fillers. Non-limiting examples of conductive polymers that can be used in the sealing layer include PEDOT-PSS, polyacetylene, polyphenylene sulfide, polyphenylene vinylene, or combinations thereof. The sealing layer may also comprise a benefit agent, which is the same or different that a benefit agent included in the medium of the microcells. The benefit agent may be incorporated in the sealing layer when the sealing layer composition is prepared and before the sealing layer is used during the preparation of the benefit agent delivery system. The horizontal cross section of the microcells may have different shapes, for example, square, round, or polygonal, such as a honeycomb structure. The sealing layer must be permeable by the benefit agent.

The liquid mixture contained in the microcell layer comprises reverse micelles in a hydrophobic liquid. The reverse micelles are stabilized by an ionic surfactant (anionic surfactant or cationic surfactant) or stabilizing particles. The internal phase of the reverse micelle comprises the benefit agent in a polar liquid. The reverse micelles may have average diameter of from 10 nm to 20 µm, or from 10 nm to 10 µm, or from 100 nm to 8 µm, or from 500 nm to 5 µm, or from 800 nm to 2 µm.

The weight percent of the benefit agent may be more than 0.01 weight percent, or more than 0.1 weight percent, or more than 1 weight percent, or more than 4 weight percent by weight of the liquid mixture. The liquid mixture may comprise from 0.001 weight percent to 50 weight percent, or from 0.01 weight percent to 40 weight percent, or from 0.01 weight percent to 25 weight percent, or form 0.1 weight percent to 25 weight percent, or from 0.5 weight percent to 20 weight percent of the benefit agent by weight of the liquid mixture.

The hydrophobic liquid may be a water-immiscible liquid that may comprise one or more compounds. The hydrophobic liquid may be a liquid having a surface tension that is lower than 30 dyne/cm. The hydrophobic liquid may comprise a silicone fluid, a hydrocarbon, an ester, an alcohol, an amide, a carboxylic acid, and other organic compounds. For example, the hydrophobic liquid may comprise alkanes such as heptane, octane or Isopar® solvents from Exxon Chemical Company, nonane, decane and their isomers, cycloalkanes such as cyclohexane and decalin, alkylbezenes, such as mono- or di-$C_{1-6}$ alkyl benzenes, alkyl esters, such as ethyl acetate, isobutyl acetate and the like, alkyl alcohols, such as isopropanol and the like and their isomers. It is preferable that the hydrophobic liquid comprises a biocompatible, non-polar compound, such as natural oil. The natural oil may be a vegetable oil, a fruit oil or a nut oil.

The weight percent of the hydrophobic liquid may be more than 40 weight percent, or more than 50 weight percent, or more than 70 weight percent, or more than 80 weight percent, or more than 90 weight percent, or more than 95 weight percent by weight of the liquid mixture. The liquid mixture may comprise from 50 weight percent to 99 weight percent, or from 60 weight percent to 97 weight percent, or from 70 weight percent to 95 weight percent, or form 75 weight percent to 92 weight percent, or from 80 weight percent to 90 weight percent of hydrophobic liquid by weight of the liquid mixture. The weight ratio of polar solvent to the hydrophobic liquid of the liquid mixture may be from 1:1 to 1:50, or from 1:1.5 to 1:30, or from 1:2 to 1:20.

The polar liquid of the liquid mixture, which is included in the plurality of microcells of the benefit agent delivery system, may be a liquid that is immiscible in the hydrophobic liquid. It may comprise one or more compounds. The polar liquid may be a liquid having a surface tension higher than 30 dyne/cm. The hydrophobic liquid may be aqueous, that is, it may comprise water or a combination of water and a water-miscible solvent. Non-limiting examples of water-miscible solvents include acetic acid, propanoic acid, butyric acid, acetone, dimethylsulfoxide, ethanol, 1-propanol, 2-propanol, 1,2-propanediol, 1,3-propanediol, 2,2-propanediol, 1,2-butanediol, 1,3-butanediol, 1,4-butanediol, 2,3-butanediol, 1,3-pentanediol, 1,5-pentanediol, 2-methyl-2,4-pentanediol, ethylene glycol, diethylene glycol, propylene glycol, dipropylene glycol, tripropylene glycol, glycerol, triethylene glycol, 2-butoxyethanol, tetrahydrofurane, ethylene carbonate, diethanolamine, dimethoxyethane, ethylamine, methyl diethanolamine, and N-methyl-2-pyrolidone. The polar liquid may be aqueous or non-aqueous. That is, the polar liquid may contain water or water and water-miscible organic liquid or it may not contain water, but only one or more water-miscible organic liquids. The polar liquid may also contain an aqueous buffer. The buffer may be necessary for providing a pH environment in which the benefit agent is stable. The buffer may also contribute to keeping the benefit agent more soluble in the polar liquid, enhancing its effective delivery through the porous second electrode layer.

The weight percent of the polar liquid may be more than 1 weight percent, or more than 2 weight percent, or more than 3 weight percent, or more than 5 weight percent, or more than 10 weight percent, or more than 12 weight percent by weight of the liquid mixture. The liquid mixture may comprise from 1 weight percent to 40 weight percent, or from 2 weight percent to 30 weight percent, or from 5 weight percent to 25 weight percent, or form 10 weight percent to 23 weight percent, or from 12 weight percent to 20 weight percent of the polar liquid by weight of the liquid mixture. In the case where the polar liquid is a combination of water and a water-miscible liquid, the water may be from 1 weight percent to 99.9 weight percent, or from 5 weight percent to 98 percent, or from 10 percent to 95 weight percent, or from 20 weight percent to 92 weight percent by weight of the polar liquid, whereas the water-miscible liquid may be from 0.1 weight percent to 99 weight percent, or from 2 weight percent to 95 weight percent, or from 5 weight percent to 90 weight percent, or from 8 weight percent to 80 weight percent by weight of the polar liquid.

In an embodiment of the present invention, the liquid mixture comprises reverse micelles in a hydrophobic liquid, wherein the reverse micelles are formed from a polar liquid, an anionic or a cationic surfactant, and a benefit agent. Thus, the micelles may have negative or positive charges.

In the case where anionic surfactants are used to form the reverse micelles, the reverse micelles have negative charges. This means that if a first voltage is applied across a microcell of the benefit delivery system via the first electrode and the porous second electrode, wherein the porous second electrode is positive, the negatively charged reversed micelles would migrate towards the porous second electrode. As a result, the concentration of reverse micelles located adjacent to the porous second electrode would increase, the diffusion of benefit agents through the porous second electrode layer would increase, causing an increase in the rate of release of the benefit agent from the benefit agent delivery system compared to the rate of release of the benefit agent from the benefit agent delivery system when no voltage is applied via the first electrode and the porous second electrode. On the contrary, if a second voltage is applied across a microcell of the benefit delivery system via the first electrode and the porous second electrode, wherein the porous second electrode is negative and the first electrode is positive, the negatively charged reversed micelles would migrate towards the first electrode. As a result, the concentration of reverse micelles located adjacent to the porous second electrode would decrease, the diffusion of benefit agents through the porous second electrode layer would decrease, causing an decrease of the rate of release of the benefit agent from the benefit agent delivery system compared to the rate of release of the benefit agent from the benefit agent delivery system when no voltage is applied via the first electrode and the porous second electrode.

In the case where cationic surfactants are used to form the reverse micelles, the reverse micelles have positively charges. This means that if a second voltage is applied across a microcell of the benefit delivery system via the first electrode and the porous second electrode, wherein the porous second electrode is negative, the positively charged reversed micelles would migrate towards the porous second electrode. As a result, the concentration of reverse micelles located adjacent to the porous second electrode would increase, the diffusion of benefit agents through the porous second electrode layer would increase, causing an increase in the rate of release of the benefit agent from the benefit agent delivery system compared to the rate of release of the benefit agent from the benefit agent delivery system when no voltage is applied via the first electrode and the porous second electrode. On the contrary, if a first voltage is applied across a microcell of the benefit delivery system via the first electrode and the porous second electrode, wherein the porous second electrode is positive and the first electrode is negative, the positively charged reversed micelles would migrate towards the first electrode. As a result, the concentration of reverse micelles located adjacent to the porous second electrode would decrease, the diffusion of benefit agents through the porous second electrode layer would decrease, causing an decrease of the rate of release of the benefit agent from the benefit agent delivery system compared to the rate of release of the benefit agent from the benefit agent delivery system when no voltage is applied via the first electrode and the porous second electrode.

The liquid mixture may also comprise, in addition to the anionic or the cationic surfactant, a nonionic surfactant, an amphoteric surfactant, a zwitterionic surfactant, or a combination thereof. Non-limiting examples of nonionic, amphoteric, and zwitterionic surfactants include, for example, polyoxyethylene (20) sorbitan monolaurate (Tween® 20, e.g. from Sigma-Aldrich), polyoxyethylene (20) sorbitan monopalmitate (Tween® 40), polyoxyethylene (20) sorbitan monooleate (Tween® 80), poloxamer 188, polyoxyethylene-polyoxypropylene block copolymer (Pluronic® F-68, e.g. from Sigma-Aldrich), polyethyleneglycol 660-12-hydroxystearate (Solutol® HS 15, BASF), cocamidopropyl betaine, linoleyl betaine, myristyl betaine, cetyl betaine, and Aerosol® OT (Dioctyl sulfosuccinate sodium salt supplied by Solvay).

The liquid mixture, which is included in the plurality of microcells of the benefit agent delivery system, may also comprise additives, such as charge control agents, rheology modifiers, and chelants. Rheology modifiers are compounds, typically polymeric materials, which adjust the viscosity of the medium to the desired value. A chelant is a compound, which is able to chelate metal cations. Non-limiting example of chelants include ethylenediaminetetraacetic acid (EDTA), ethylene diamine disuccinic acid (EDDS), aminotri(methylenephosphonic acid) (ATMP), 1,3-diamino-2-propanoltetraacetic acid (DTPA), dipicolinic acid (DPA), and ethylenediamine-N,N'-bis(2-hydroxyphenylacetic acid) (EDDHA). The medium may contain from 0.001 weight % to 5 weight %, or from 0.01 weight % to 3 weight %, or from 0.1 weight % to 1 weight % of a chelant by weight of the medium.

The liquid mixture, which is included in the plurality of microcells of the benefit agent delivery system, may also comprise a charge control agent. The charge control agent may participate in the reverse micelles and increase their charge, contributing to the movement of the reverse micelles towards the porous second electrode and the delivery of the benefit agent from the benefit agent delivery system. Non-limiting examples of charge control agents include, Solsperse 17000 (active polymeric dispersant), Solsperse 9000 (active polymeric dispersant), OLOA® 11000 (succinimide ashless dispersant), Unithox 750 (ethoxylates), Span 85 (sorbitan trioleate), Petronate L (sodium sulfonate), Alcolec LV30 (soylecithin), Petrostep B100 (petroleum sulfonate) or B70 (barium sulfonate), Aerosol OT, polyisobutylene derivatives and poly(ethylene co-butylene) derivatives.

As mentioned above, the surfactant of the liquid mixture, which is included in the plurality of microcells of the benefit agent delivery system, may be as an anionic surfactant or a cationic surfactant. Non-limiting examples of anionic surfactants include, for example, fatty acid soaps, sodium lauryl sulfate, sodium lauryl ether sulfate, alkyl benzene sulfonate, mono- and di-alkyl acid phosphates and sodium fatty acyl isethionate. Non-limiting examples of cationic surfactants include, for example, quaternary ammonium salts comprising fatty groups, such as stearamidopropyl dimethyl ammonium chloride, stearamidopropyl dimethyl ammonium lactate, dilauryl dimethyl ammonium chloride, distearyl dimethyl ammonium chloride, dimyristyl dimethyl ammonium chloride, and dipalmityl dimethyl ammonium chloride. Polymeric materials, which contain one or more hydrophobic functional groups and one or more hydrophilic groups, are also considered surfactants herein.

Surfactants reduce the surface tension between two liquids (interfacial tension). Thus, the surfactant contributes to the formation of the reverse micelle in the hydrophobic liquid of the liquid mixture. Surfactants are organic compounds that are amphiphilic, which means that they contain both one or more hydrophobic functional groups (tail) and one or more hydrophilic functional groups (head). The surfactant molecules of the liquid mixture stabilize the reverse micelles in the hydrophobic liquid. Each polar liquid droplet of a reverse micelle is surrounded by numerous surfactant molecules. The hydrophilic functional groups of the surfactants of the liquid mixture face toward the polar liquid droplet of the reverse micelle, whereas the hydrophobic functional groups of the surfactants are aligned and extended towards the hydrophobic liquid, which is the continuous phase of the reverse micelles.

The weight percent of the total surfactants in the liquid mixture, which is included in the plurality of microcells of the benefit agent delivery system, may be more than 1 weight percent, or more than 0.1 weight percent, or more than 0.2 weight percent, or more than 0.3 weight percent, or more than 0.4 weight percent of surfactant by weight of the liquid mixture. The liquid mixture may comprise from 0.1 weight percent to 5 weight percent, or from 0.2 weight percent to 4 weight percent, or from 0.3 weight percent to 2 weight percent, or form 0.4 weight percent to 1 weight percent, or from 0.5 weight percent to 0.8 weight percent of the surfactant or surfactants by weight of the liquid mixture.

An example of a benefit agent delivery system of the present invention is shown in FIG. 1A. The benefit agent delivery system may comprise a backing layer 110, a first electrode layer 120, a microcell layer comprising a plurality of microcells (130A, 130B, 130C), a porous second electrode layer 150, and a release sheet 160. Microcell walls 135 separate the microcells from each other. Each microcell includes a liquid mixture. The liquid mixture comprises reverse micelles 145 in hydrophobic liquid 140. The reverse micelles in the hydrophobic liquid are formed from a polar liquid, a surfactant, and a benefit agent. The plurality of microcell is an array that is formed from a polymer matrix, which is described in more detail below. The backing layer 110 provide structural support. The backing layer may have thickness of from 1 μm to 5 mm, or from 25 μm to 300 μm.

The plurality of microcells (130A, 130B, 130C) are disposed between a first electrode layer 120 and a porous second electrode layer 150. The porous second electrode layer 150 may be a mesh from a metallic material having rows and columns. The porous second electrode layer may also comprise or a plurality of electrodes 155. Alternatively, the porous second electrode layer may comprise a single electrode and the first electrode layer may comprise a plurality of electrodes. The system may additionally comprise an adhesive layer between the porous second electrode layer 150 and the release sheet 160.

Figure 1B:
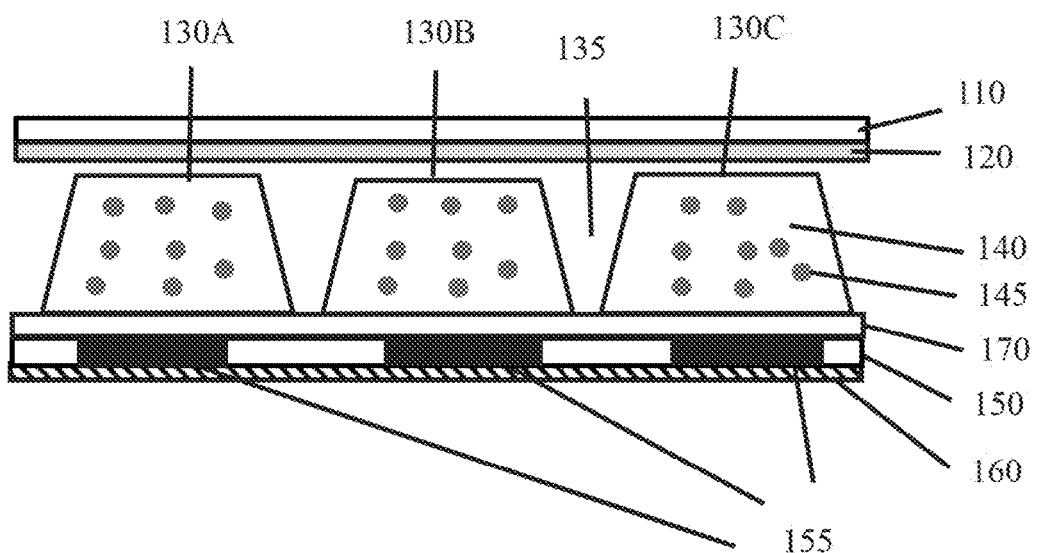
FIG. 1B illustrates an example of a benefit agent delivery system comprising a first electrode layer, a plurality of microcells, each microcell containing reverse micelles in a hydrophobic liquid, a sealing layer, and a porous second electrode layer; the sealing layer spans the first opening of each microcell.

FIG. 1B shows another example of a benefit agent delivery system. In this example, a sealing layer 170 is disposed between the microcell layer and the porous second electrode layer 150. There may be also an adhesive layer between the sealing layer 170 and the porous second electrode layer 150. The adhesive layer may be porous and it may have thickness of from 200 nm to 5 mm, or from 1 μm to 100 μm.

In the example of the benefit agent delivery system illustrated by FIG. 1B, the liquid mixture, which is included in the plurality of microcells 130A, 130B, and 130C, is not in direct contact with the porous electrode layer 150, but the sealing layer 170 spans the first opening of each microcell.

Figure 1C:
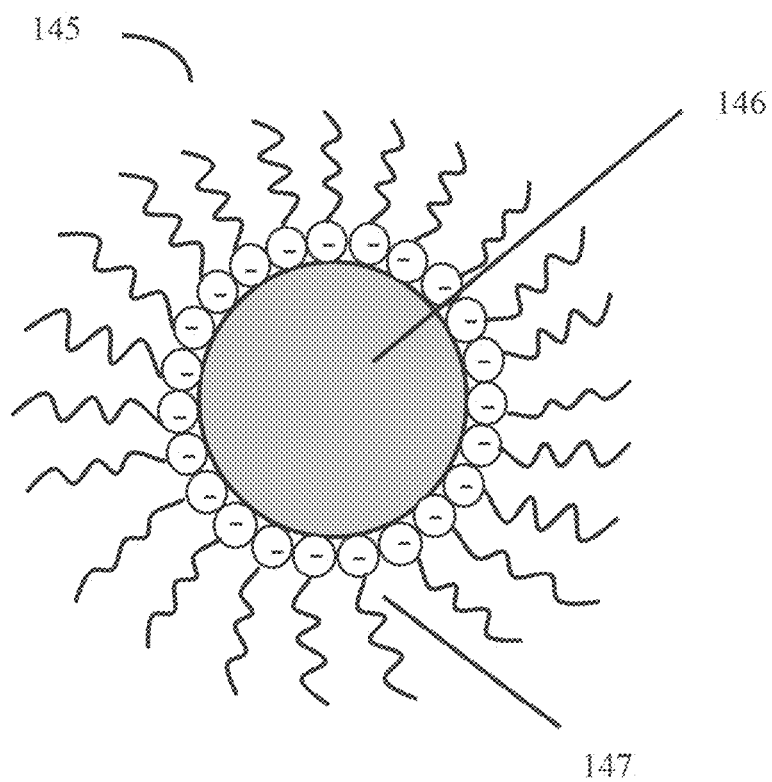
FIG. 1C illustrates the structure of a reverse micelle that is stabilized by anionic surfactants.
Figure 1D:
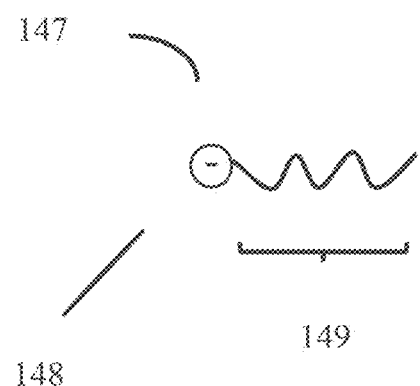
FIG. 1D illustrates the structure of an anionic surfactant.

As described above, the liquid mixture in the plurality of microcells of the benefit agent delivery system comprises reverse micelles in a hydrophobic liquid. A typical structure of a reverse micelle 145 is illustrated in FIG. 1C. The reverse micelle comprises a polar internal phase 146 that includes the benefit agent(s), and anionic surfactant molecules 147 that surround the internal phase of the reverse micelle. The structure of the surfactant 147 can be illustrated in FIG. 1D. Each surfactant molecule comprises a polar part 148 (head) and a nonpolar part 149 (tail). The head 148 of surfactant 145 comprises hydrophilic functional anionic group(s) and the tail 149 comprises hydrophobic functional group(s). The surfactant illustrated in FIG. 1D comprises one head and one tail. However, there are surfactants that comprises multiple heads and/or multiple tails. In reverse micelles, the heads of the surfactants face towards the polar internal phase droplet and the tail of the surfactants are aligned towards the hydrophobic liquid of the continuous phase of the reverse micelle, as shown in FIG. 1C, stabilizing the reverse micelles in the hydrophobic liquid.

Figure 1E:
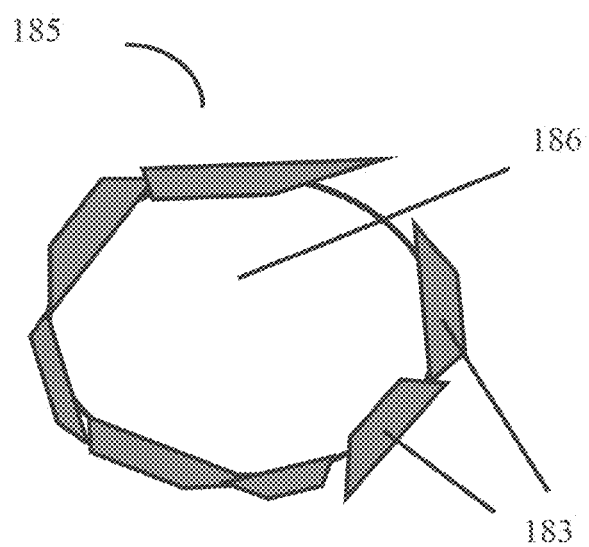
FIG. 1E illustrates the structure of a reverse micelle that is stabilized by stabilizing particles.

FIG. 1E illustrates a reversed micelle 185 wherein the hydrophilic liquid 186 is stabilized in a hydrophobic liquid by stabilizing particles 183. This is the case of a Pickering emulsion, or more specifically a Pickering reverse micelle in this case. In the present invention, the liquid mixture may comprise reverse micelles that are stabilized by both surfactants (anionic or cationic) and also by stabilizing particles. Typically, stabilizing particles are positioned between the dispersed phase and the continuous phase of the reverse micelles. Reverse micelles that are stabilized both by anionic or cationic and stabilizing particles are charged, because of the ionic nature of the surfactants. Thus, the movement of the reverse micelles can be controlled by the electric field that is applied across a microcell.

In the case where anionic surfactants are used to form the reverse micelles, the reverse micelles have negative charges. This means that if a first voltage is applied across a microcell of the benefit delivery system via the first electrode and the porous second electrode, wherein the porous second electrode is positive, the negatively charged reversed micelles would migrate towards the porous second electrode. As a result, the concentration of reverse micelles located adjacent to the porous second electrode would increase, the diffusion of benefit agents through the porous second electrode layer would increase, causing an increase in the rate of release of the benefit agent from the benefit agent delivery system compared to the rate of release of the benefit agent from the benefit agent delivery system when no voltage is applied via the first electrode and the porous second electrode. On the contrary, if a second voltage is applied across a microcell of the benefit delivery system via the first electrode and the porous second electrode, wherein the porous second electrode is negative and the first electrode is positive, the negatively charged reversed micelles would migrate towards the first electrode. As a result, the concentration of reverse micelles located adjacent to the porous second electrode would decrease, the diffusion of benefit agents through the porous second electrode layer would decrease, causing an decrease of the rate of release of the benefit agent from the benefit agent delivery system compared to the rate of release of the benefit agent from the benefit agent delivery system when no voltage is applied via the first electrode and the porous second electrode.

Figure 2A:
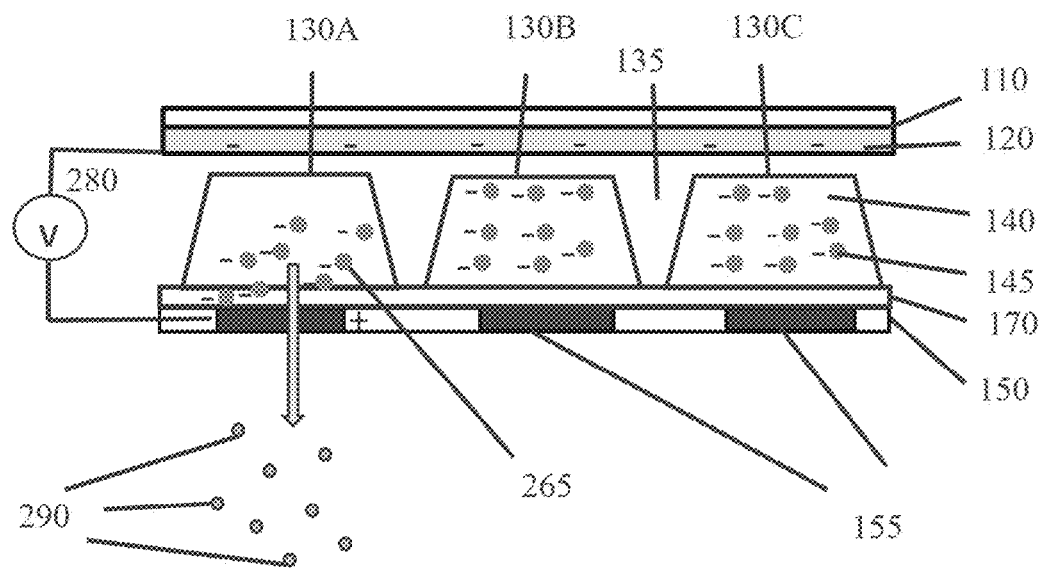
FIG. 2A illustrates an example of a benefit agent delivery system comprising a first electrode layer, a plurality of microcells, each microcell comprising reverse micelles in a hydrophobic liquid that are stabilized by anionic surfactant, a sealing layer, and a porous second electrode layer; upon application of a voltage across a microcell that causes the reverse micelles to migrate towards the porous second electrode layer, the rate of release of the benefit agent of the microcell through the porous second electrode layer increases.

FIG. 2A shows the benefit agent delivery system similar to the one illustrated in FIG. 1B after the activation of a microcell by the application of electric field. The benefit agent delivery system of FIG. 2A comprises a liquid mixture comprising reverse micelles 145 in hydrophobic liquid 140. The reverse micelles in this example are stabilized by anionic surfactants. Thus, reverse micelles are shown as negatively charged. The benefit agent delivery system of FIG. 2B comprises a voltage source 280 that electrically couples the first electrode layer 120 with the porous second electrode layer. The activation of microcell 130A takes place via the application of a first voltage via the voltage source 280 across microcell 130A. The applied first voltage results in the porous second electrode at microcell 130A being positive and the first electrode 120 being negative. The fact that reverse micelles 265 are negatively charged and the porous second electrode at microcell 130A is positive causes the reverse micelles 265 of microcell 130A to migrate towards the porous second electrode. This increases the concentration of reverse micelles adjacent to the sealing layer at microcell 130A, which increases the diffusion of reverse micelles 265 through the sealing layer and porous second electrode layer and increases the rate of release of the benefit agent 290 through the porous second electrode layer compared to the rate of release of the benefit agent through the porous second electrode layer when no voltage is applied. The rate of release of the benefit agent through the porous second electrode layer may be more than 10%, or more than 25%, or more than 50%, or more than 75% or more than 90% compared to the rate of release of the benefit agent through the porous second electrode layer before the application of the electric field.

Figure 2B:
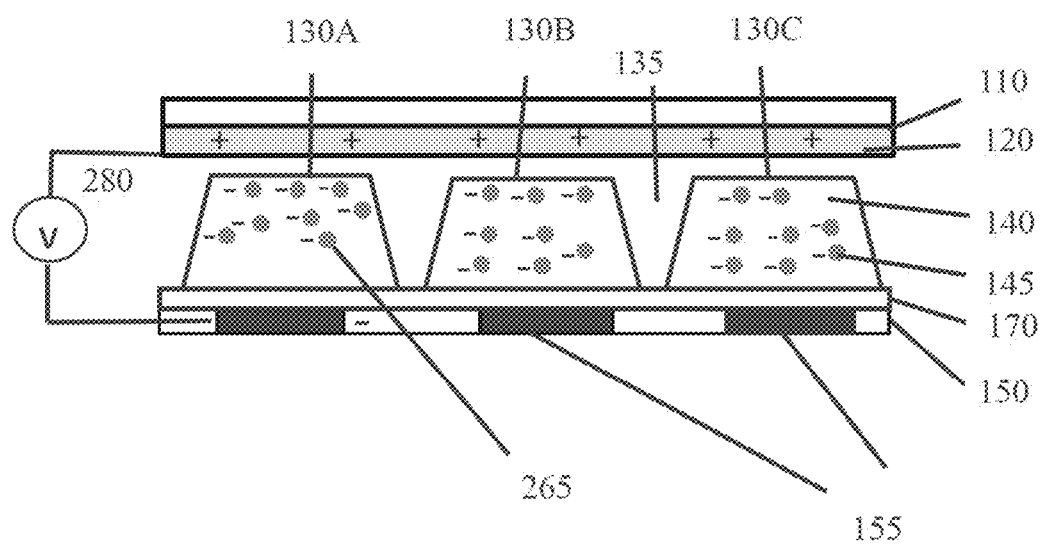
FIG. 2B illustrates an example of a benefit agent delivery system comprising a first electrode layer, a plurality of microcells, each microcell comprising reverse micelles in a hydrophobic liquid, which are stabilized by anionic surfactant, a sealing layer, and a porous second electrode layer; upon application of a second voltage across a microcell that causes the reverse micelles to migrate away from the porous second electrode layer, the rate of release of the benefit agent of the microcell through the porous second electrode layer decreases.

FIG. 2B shows the benefit agent delivery system illustrated in FIG. 1B after application of electric field across microcell 130A via voltage source 280. In this example, though, a second voltage is applied across microcell 130A. The applied second voltage results in the porous second electrode at microcell 130A being negative and the first electrode 120 being positive. The fact that reverse micelles 265 are negatively charged and the first electrode 120 is positive causes reverse micelles of microcell 130A to migrate towards the first electrode and away from the porous second electrode layer. This decreases the concentration of reverse micelles 265 adjacent to the sealing layer at microcell 130A, which decreases the diffusion of reverse micelles 265 through the sealing layer and porous second electrode layer and decreases the rate of release of the benefit agent through the porous second electrode layer compared to the rate of release of the benefit agent through the porous second electrode layer when no voltage is applied. The rate of release of the benefit agent through the porous second electrode layer may be less than 10%, or less than 25%, or less than 50%, or less than 75% or less than 90% compared to the rate of release of the benefit agent through the porous second electrode layer before the application of the electric field.

In the case where reverse micelles comprise both ionic surfactants and stabilizing particles, the stabilizing particles may be organic or inorganic particles. Non-limiting examples of stabilizing particles include silica, iron oxide, alumina, other metal oxides, clay, natural or synthetic phyllosilicate, carbon black, carbon nanotubes, polymeric particles, chitosan, cyclodextrin, starch, natural proteins, and other particles. Stabilizing particles, which comprise inorganic materials, may have a surface that is hydrophobically modified. Stabilizing reverse emulsions by such particles offer the advantage of higher biocompatibility of particles in comparison to surfactant molecules.

The stabilizing particles may have various shapes including spheres, plates, cylinders, ellipsoid, and other shapes. The stabilizing particles may have a variety of sizes. For example, the stabilizing particles may have average size of from 10 nm to 2 μm, or from 10 nm to 800 nm, or from 100 nm to 300 nm. In this case, the average size refers to the largest dimension of the particle.

The weight percent of the stabilizing particles in the liquid mixture, which is included in the plurality of microcells of the benefit agent delivery system, may be more than 1 weight percent, or more than 0.1 weight percent, or more than 0.2 weight percent, or more than 0.3 weight percent, or more than 0.4 weight percent of surfactant by weight of the liquid mixture. The liquid mixture may comprise from 0.1 weight percent to 20 weight percent, or from 0.2 weight percent to 10 weight percent, or from 0.3 weight percent to 5 weight percent, or form 0.4 weight percent to 3 weight percent, or from 0.5 weight percent to 1 weight percent of the stabilizing particles by weight of the liquid mixture.

Figure 3:
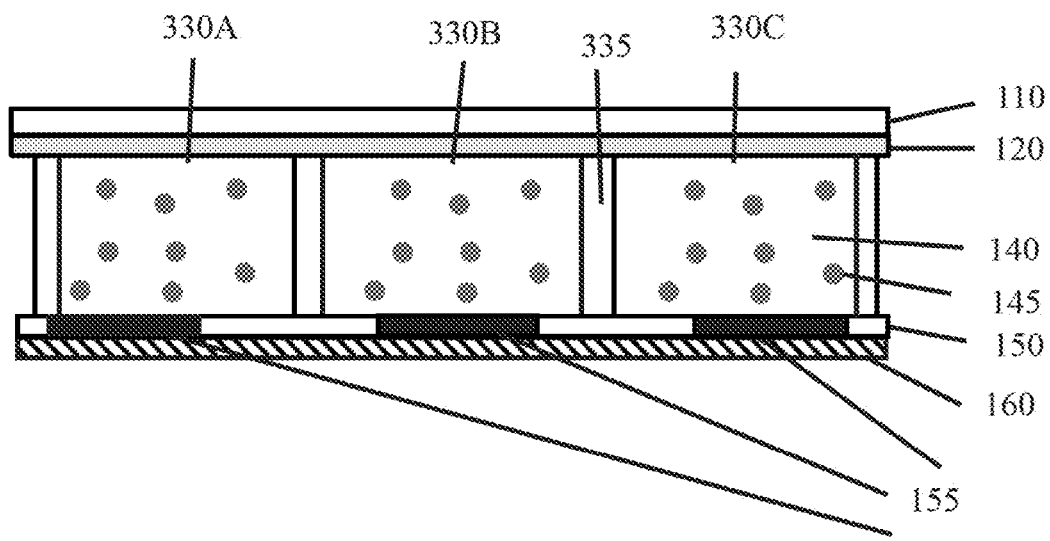
FIG. 3 illustrates an example of a benefit agent delivery system comprising a first electrode layer, a plurality of microcells, each of which has two openings, and a porous second electrode layer; the first electrode layer spans the second opening of each microcell, and the porous second electrode layer spans the first opening; the plurality of microcells contain reverse micelles in a hydrophobic liquid having a benefit agent.

Another example of a benefit agent delivery system of the present invention is shown in FIG. 3. The benefit agent delivery system may comprise a backing layer 110, a first electrode layer 120, a microcell layer comprising a plurality of microcells (330A, 330B, 330C), a porous second electrode layer 150, and a release sheet 160. In this example, each microcell of the plurality of microcells (330A, 330B, 330C) has two openings, a first opening and a second opening. The first opening and the second opening are at opposite sides of the microcell. The first electrode layer 120 spans the second opening of each microcell and the porous second electrode layer 150 spans the first opening of each microcell. Microcell walls 335 separate the microcells from each other. Each microcell includes a liquid mixture. The liquid mixture comprises reverse micelles 145 in hydrophobic liquid 140. The reverse micelles in the hydrophobic liquid are formed from a polar liquid, an anionic or a cationic surfactant, and a benefit agent. In this example, both the first electrode layer 120 and the porous second electrode layer 150 are in contact with the liquid mixture that is included in the plurality of microcells.

Figure 4:
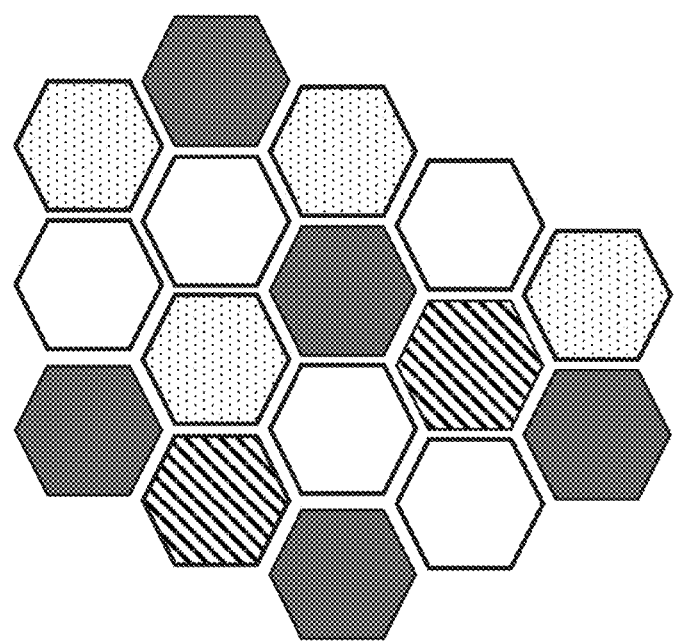
FIG. 4 illustrates an example of a benefit agent delivery system comprising a plurality of different types of benefit agents and/or a plurality of concentrations of benefit agents in the same delivery system.

The microcell structure of the invention lends itself to making arrays of differing benefit agents, or arrays of different concentrations, as illustrated in FIG. 4. Because the microcells can be individually activated with an active matrix of electrodes, it is possible to provide varying benefit agents on demand and to produce complex dosing profiles. Using injection with inkjet or other fluidic systems, individual microcells can be filled to enable a variety of different benefit agents to be included in a benefit agent delivery system. For example, a system of the invention may include nicotine at four different concentrations, thereby allowing different dosages to be delivered at different times during the day. For example, shortly after waking up the most concentrated dose may be delivered (dark gray), followed by a much lower taper dose during the day (speckled), until the time that a user needs another more concentrated dose. It is possible to include different benefit agents in the same microcell. For example, the system illustrated in FIG. 4 may also include an analgesic (stripes) to reduce swelling and itching in the area of the skin that is in contact with the delivery system. Of course, a variety of combinations are possible, and varying microcells might include pharmaceuticals, nutraceuticals, nutrients, adjuvants, vitamins, vaccines, hormones, cosmetic agents, fragrances, preservatives, etc. Furthermore, the arrangement of the microcells may not be distributed. Rather, the microcells may be filled in clusters, which makes filling and activation more straightforward. In other embodiments, smaller microcell arrays may be filled with the same medium, i.e., having the same benefit agent at the same concentration, and then the smaller arrays assembled into a larger array to make a delivery system of the invention.

Figure 5:
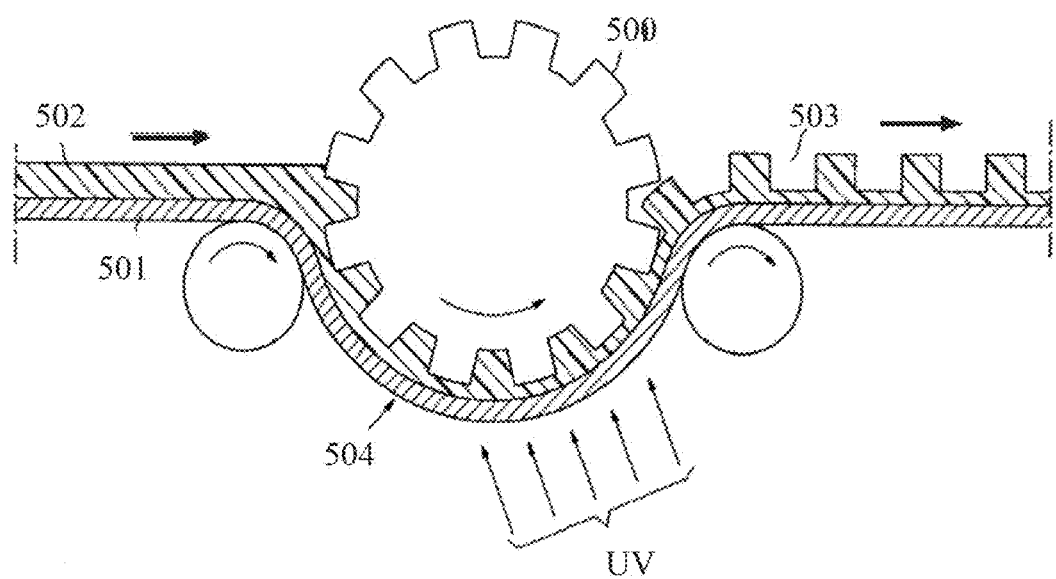
FIG. 5 shows a method for making microcells for the invention using a roll-to-roll process.

Techniques for constructing microcells. Microcells may be formed either in a batch process or in a continuous roll-to-roll process as disclosed in U.S. Pat. No. 6,933,098. The latter offers a continuous, low cost, high throughput manufacturing technology for production of compartments for use in a variety of applications including benefit agent delivery and electrophoretic displays. Microcell arrays suitable for use with the invention can be created with microembossing, as illustrated in FIG. 5. A male mold 500 may be placed either above the web 504 or below the web 504 (not shown); however, alternative arrangements are possible. For examples, please see U.S. Pat. No. 7,715,088, which is incorporated herein by reference in its entirety. A conductive substrate may be constructed by forming a conductor film 501 on polymer substrate that becomes the backing layer for a device. A composition comprising a thermoplastic, thermoset, or a precursor thereof 502 is then coated on the conductor film. The conductor film serves as the first electrode layer of the benefit agent delivery system. The thermoplastic or thermoset precursor layer is embossed at a temperature higher than the glass transition temperature of the thermoplastics or thermoset precursor layer by the male mold in the form of a roller, plate or belt.

The thermoplastic or thermoset precursor for the preparation of the plurality of microcells may be multifunctional acrylate or methacrylate, vinyl ether, epoxide and oligomers or polymers thereof, and the like. A combination of multifunctional epoxide and multifunctional acrylate is also very useful to achieve desirable physico-mechanical properties. A crosslinkable oligomer imparting flexibility, such as urethane acrylate or polyester acrylate, may be added to improve the flexure resistance of the embossed microcells. The composition may contain polymer, oligomer, monomer and additives or only oligomer, monomer and additives. The glass transition temperatures (or $T_g$) for this class of materials usually range from about $-70°$ C. to about $150°$ C., preferably from about $-20°$ C. to about $50°$ C. The microembossing process is typically carried out at a temperature higher than the $T_g$. A heated male mold or a heated housing substrate against which the mold presses may be used to control the microembossing temperature and pressure.

As shown in FIG. 5, the mold is released during or after the precursor layer is hardened to reveal an array of microcells 503. The hardening of the precursor layer may be accomplished by cooling, solvent evaporation, cross-linking by radiation, heat or moisture. If the curing of the thermoset precursor is accomplished by UV radiation, UV may radiate onto the transparent conductor film from the bottom or the top of the web as shown in the two figures. Alternatively, UV lamps may be placed inside the mold. In this case, the mold must be transparent to allow the UV light to radiate through the pre-patterned male mold on to the thermoset precursor layer. A male mold may be prepared by any appropriate method, such as a diamond turn process or a photoresist process followed by either etching or electroplating. A master template for the male mold may be manufactured by any appropriate method, such as electroplating. With electroplating, a glass base is sputtered with a thin layer (typically 3000 Å) of a seed metal such as chrome inconel. The mold is then coated with a layer of photoresist and exposed to UV. A mask is placed between the UV and the layer of photoresist. The exposed areas of the photoresist become hardened. The unexposed areas are then removed by washing them with an appropriate solvent. The remaining hardened photoresist is dried and sputtered again with a thin layer of seed metal. The master is then ready for electroforming. A typical material used for electroforming is nickel cobalt. Alternatively, the master can be made of nickel by electroforming or electroless nickel deposition. The floor of the mold is typically between about 50 to 400 microns. The master can also be made using other microengineering techniques including e-beam writing, dry etching, chemical etching, laser writing or laser interference as described in "Replication techniques for micro-optics", SPIE Proc. Vol. 3099, pp. 76-82 (1997). Alternatively, the mold can be made by photomachining using plastics, ceramics or metals.

Prior to applying a UV curable resin composition, the mold may be treated with a mold release to aid in the demolding process. The UV curable resin may be degassed prior to dispensing and may optionally contain a solvent. The solvent, if present, readily evaporates. The UV curable resin is dispensed by any appropriate means such as, coating, dipping, pouring or the like, over the male mold. The dispenser may be moving or stationary. A conductor film is overlaid the UV curable resin. Pressure may be applied, if necessary, to ensure proper bonding between the resin and the plastic and to control the thickness of the floor of the microcells. The pressure may be applied using a laminating roller, vacuum molding, press device or any other like means. If the male mold is metallic and opaque, the plastic substrate is typically transparent to the actinic radiation used to cure the resin. Conversely, the male mold can be transparent and the plastic substrate can be opaque to the actinic radiation. To obtain good transfer of the molded features onto the transfer sheet, the conductor film needs to have good adhesion to the UV curable resin, which should have a good release property against the mold surface.

Microcell arrays for the invention typically include a pre-formed first electrode layer, such as indium tin oxide (ITO) conductor lines; however, other conductive materials, such as silver or aluminum, may be used. The first electrode layer may be backed by or integrated into substrates such as polyethylene terephthalate, polyethylene naphthalate, polyaramid, polyimide, polycycloolefin, polysulfone, epoxy and their composites. The first electrode layer may be coated with a radiation curable polymer precursor layer. The film and precursor layer are then exposed imagewise to radiation to form the microcell wall structure. Following exposure, the precursor material is removed from the unexposed areas, leaving the cured microcell walls bonded to the conductor film/support web. The imagewise exposure may be accomplished by UV or other forms of radiation through a photomask to produce an image or predetermined pattern of exposure of the radiation curable material coated on the conductor film. Although it is generally not required, the mask may be positioned and aligned with respect to the first electrode layer, i.e., ITO lines, so that the transparent mask portions align with the spaces between ITO lines, and the opaque mask portions align with the ITO material (intended for microcell cell floor areas).

Figure 6A:
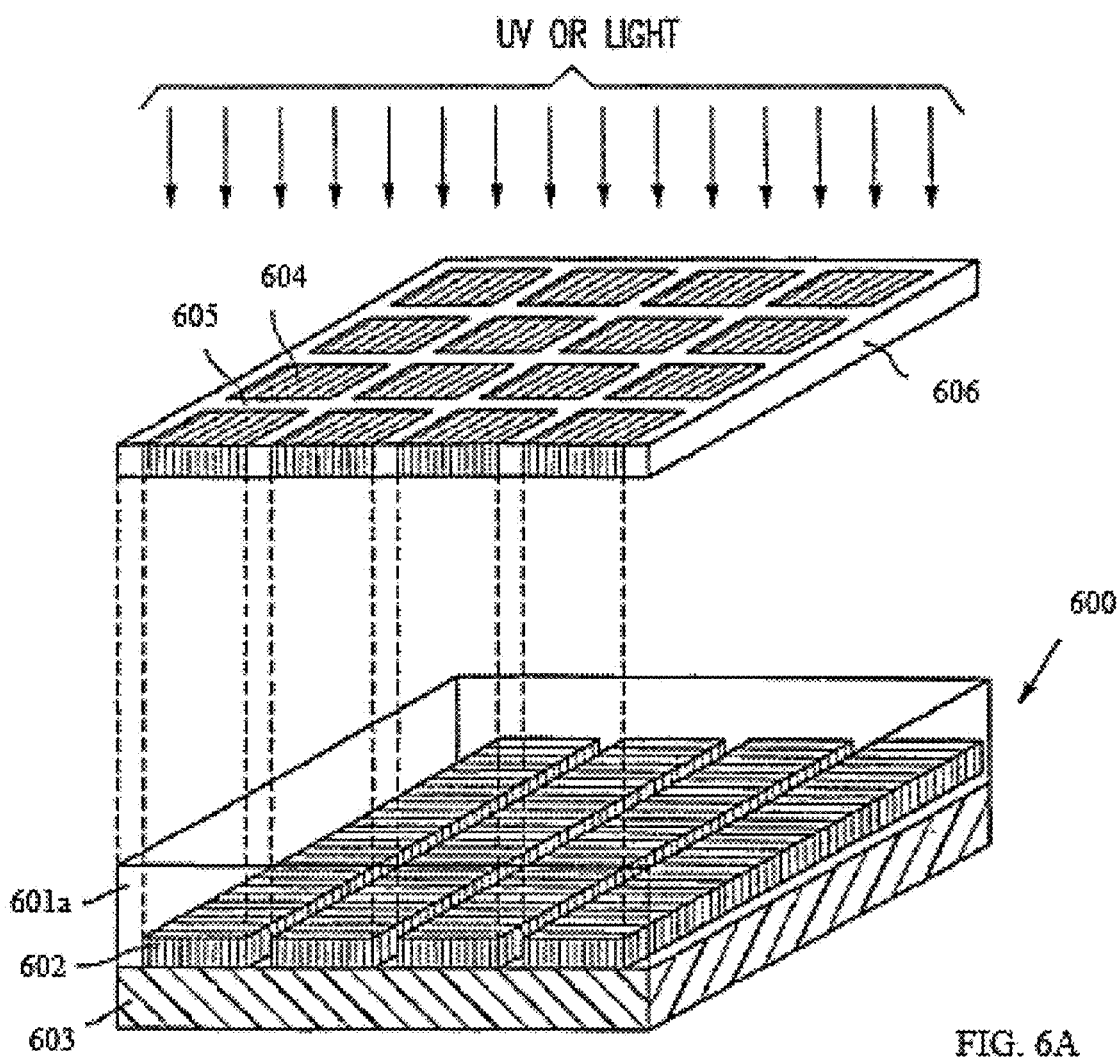
FIGS. 6A and 6B detail the production of microcells for a benefit agent delivery system using photolithographic exposure through a photomask of a conductor film coated with a thermoset precursor.
Figure 6B:
Figure 6B:
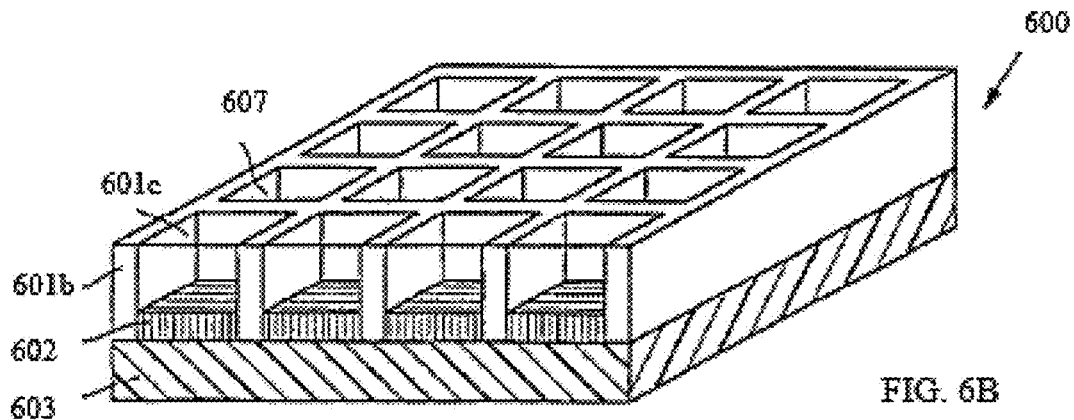

Photolithography. Microcells can also be produced using photolithography. Photolithographic processes for fabricating a microcell array are illustrated in FIGS. 6A and 6B. As shown in FIGS. 6A and 6B, the microcell array 600 may be prepared by exposure of a radiation curable material 601*a* coated by known methods onto a conductor electrode film 602 to UV light (or alternatively other forms of radiation, electron beams and the like) through a mask 606 to form walls 601*b* corresponding to the image projected through the mask 606. The base conductor film 602 is preferably mounted on a supportive substrate base web 603, which may comprise a plastic material.

In the photomask 606 in FIG. 6A, the dark squares 604 represent the opaque area and the space between the dark squares represents the transparent area 605 of the mask 606. The UV radiates through the transparent area 605 onto the radiation curable material 601*a*. The exposure is preferably performed directly onto the radiation curable material 601*a*, i.e., the UV does not pass through the substrate 603 or base conductor 602 (top exposure). For this reason, neither the substrate 603, nor the conductor 602, needs to be transparent to the UV or other radiation wavelengths employed.

As shown in FIG. 6B, the exposed areas 601b become hardened and the unexposed areas (protected by the opaque area 604 of the mask 606) are then removed by an appropriate solvent or developer to form the microcells 607. The solvent or developer is selected from those commonly used for dissolving or reducing the viscosity of radiation curable materials such as methylethylketone (MEK), toluene, acetone, isopropanol or the like. The preparation of the microcells may be similarly accomplished by placing a photomask underneath the conductor film/substrate support web and in this case the UV light radiates through the photomask from the bottom and the substrate needs to be transparent to radiation.

The photolithography methodology described in the previous three paragraphs may be utilized to manufacture the benefit agent delivery system illustrated in FIG. 3, wherein each of the plurality of microcells has two openings, a first opening and a second opening at opposite sides of the microcell, wherein the first electrode layer spans the second opening and the porous second electrode layer spans the first opening.

Figure 6C:
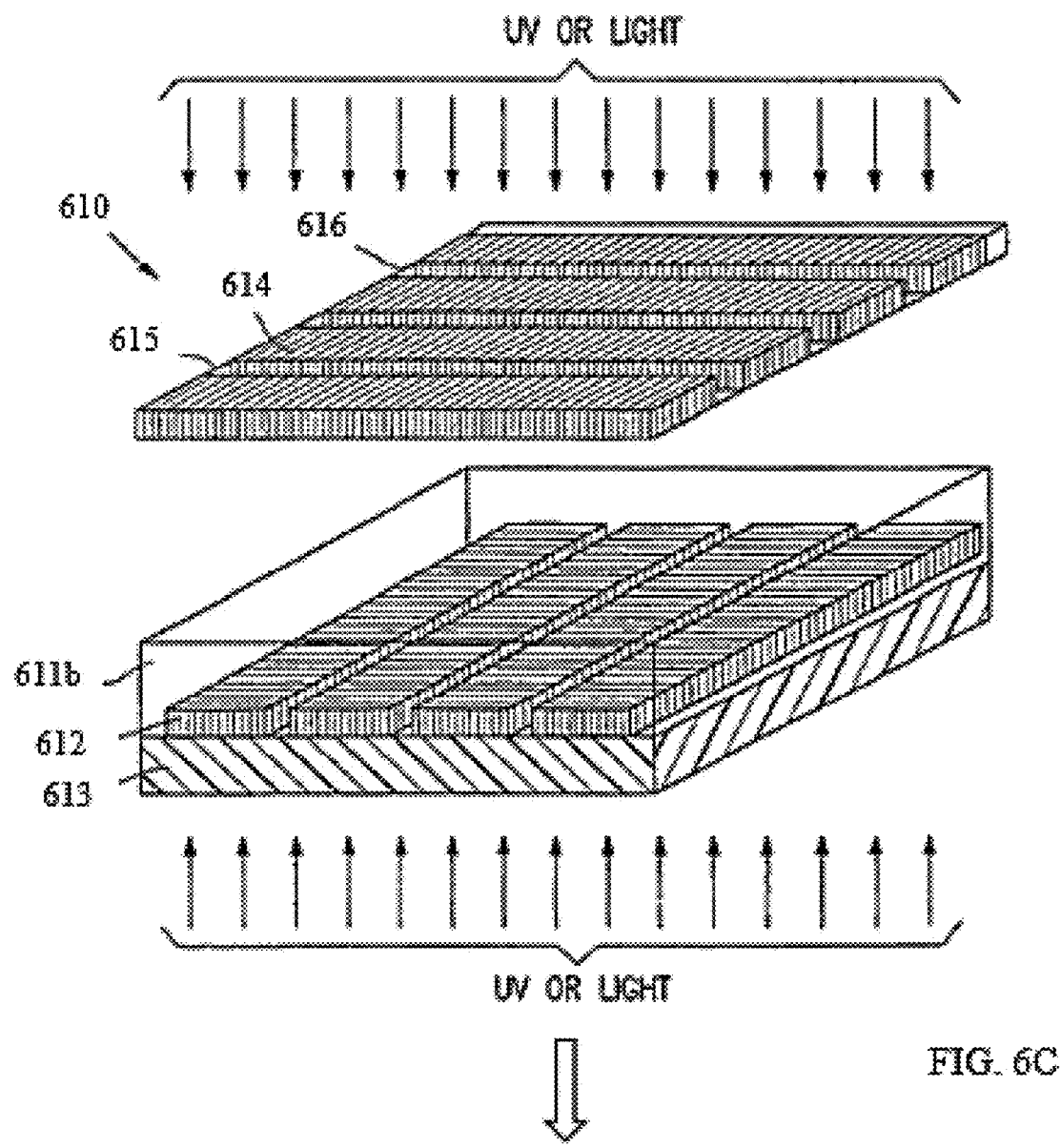
FIGS. 6C and 6D detail an alternate embodiment in which microcells for a benefit agent delivery system are fabricated using photolithography.
Figure 6D:
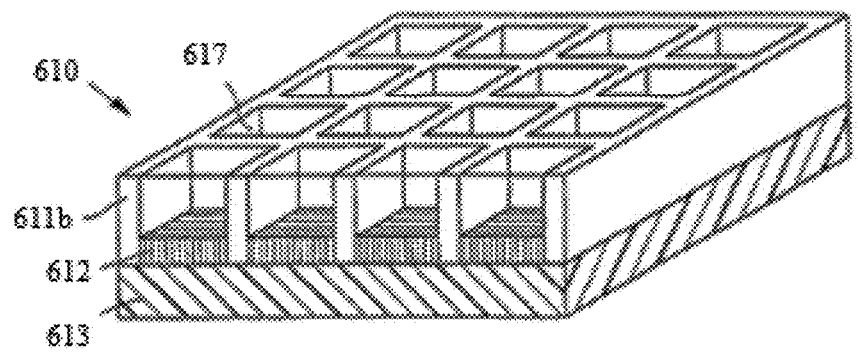

Imagewise Exposure. Still another alternative method for the preparation of the microcell array of the invention by imagewise exposure is illustrated in FIGS. 6C and 6D. When opaque conductor lines are used, the conductor lines can be used as the photomask for the exposure from the bottom. Durable microcell walls are formed by additional exposure from the top through a second photomask having opaque lines perpendicular to the conductor lines. FIG. 6C illustrates the use of both the top and bottom exposure principles to produce the microcell array 610 of the invention. The base conductor film 612 is opaque and line-patterned. The radiation curable material 611a, which is coated on the base conductor 612 and substrate 613, is exposed from the bottom through the conductor line pattern 612, which serves as the first photomask. A second exposure is performed from the "top" side through the second photomask 616 having a line pattern perpendicular to the conductor lines 612. The spaces 615 between the lines 614 are substantially transparent to the UV light. In this process, the wall material 611b is cured from the bottom up in one lateral orientation, and cured from the top down in the perpendicular direction, joining to form an integral microcell 617. As shown in FIG. 6D, the unexposed area is then removed by a solvent or developer as described above to reveal the microcells 617.

The microcells may be constructed from thermoplastic elastomers, which have good compatibility with the microcells and do not interact with the media. Examples of useful thermoplastic elastomers include ABA, and (AB)n type of di-block, tri-block, and multi-block copolymers wherein A is styrene, α-methylstyrene, ethylene, propylene or norbornene; B is butadiene, isoprene, ethylene, propylene, butylene, dimethylsiloxane or propylene sulfide; and A and B cannot be the same in the formula. The number, n, is ≥1, preferably 1-10. Particularly useful are di-block or tri-block copolymers of styrene or ox-methylstyrene such as SB (poly(styrene-b-butadiene)), SBS (poly(styrene-b-butadiene-b-styrene)), SIS (poly(styrene-b-isoprene-b-styrene)), SEBS (poly(styrene-b-ethylene/butylenes-b-styrene)) poly(styrene-b-dimethylsiloxane-b-styrene), poly((α-methylstyrene-b-isoprene), poly(α-methylstyrene-b-isoprene-b-α-methylstyrene), poly(α-methylstyrene-b-propylene sulfide-b-α-methylstyrene), poly(α-methylstyrene-b-dimethylsiloxane-b-α-methylstyrene). Commercially available styrene block copolymers such as Kraton D and G series (from Kraton Polymer, Houston, Tex.) are particularly useful. Crystalline rubbers such as poly(ethylene-co-propylene-co-5-methylene-2-norbomene) or EPDM (ethylene-propylene-diene terpolymer) rubbers such as Vistalon 6505 (from Exxon Mobil, Houston, Tex.) and their grafted copolymers have also been found very useful.

The thermoplastic elastomers may be dissolved in a solvent or solvent mixture, which is immiscible with the carrier in the microcells and exhibits a specific gravity less than that of the carrier. Low surface tension solvents are preferred for the overcoating composition because of their better wetting properties over the microcell walls and the fluid. Solvents or solvent mixtures having a surface tension lower than 35 dyne/cm are preferred. A surface tension of lower than 30 dyne/cm is more preferred. Suitable solvents include alkanes (preferably $C_{6-12}$ alkanes such as heptane, octane or Isopar solvents from Exxon Chemical Company, nonane, decane and their isomers), cycloalkanes (preferably $C_{6-12}$ cycloalkanes such cyclohexane and decalin and the like), alkylbezenes (preferably mono- or di-$C_{1-6}$ alkyl benzenes such as toluene, xylene and the like), alkyl esters (preferably $C_{2-5}$ alkyl esters such as ethyl acetate, isobutyl acetate and the like) and $C_{3-5}$ alkyl alcohols (such as isopropanol and the like and their isomers). Mixtures of alkylbenzene and alkane are particularly useful.

In addition to polymer additives, the polymer mixtures may also include wetting agents (surfactants). Wetting agents (such as the FC surfactants from 3M Company, Zonyl fluorosurfactants from DuPont, fluoroacrylates, fluoromethacrylates, fluoro-substituted long chain alcohols, perfluoro-substituted long chain carboxylic acids and their derivatives, and Silwet silicone surfactants from OSi, Greenwich, Conn.) may also be included in the composition to improve the adhesion of the layer, which spans the microcell opening (porous second electrode layer or sealing layer) to the microcells and provides a more flexible coating process. Other ingredients including crosslinking agents (e.g., bisazides such as 4,4'-diazidodiphenylmethane and 2,6-di-(4'-azidobenzal)-4-methylcyclohexanone), vulcanizers (e.g., 2-benzothiazolyl disulfide and tetramethylthiuram disulfide), multifunctional monomers or oligomers (e.g., hexanediol, diacrylates, trimethylolpropane, triacrylate, divinylbenzene, diallylphthalene), thermal initiators (e.g., dilauroryl peroxide, benzoyl peroxide) and photoinitiators (e.g., isopropyl thioxanthone (ITX), Irgacure 651 and Irgacure 369 from Ciba-Geigy) are also highly useful to enhance the physico-mechanical properties of the layer, which spans the microcell opening (porous second electrode layer or sealing layer), by crosslinking or polymerization reactions during or after the overcoating process.

After the microcells are produced, they are filled with appropriate liquid mixture or liquid mixtures. The microcell array 700 may be prepared by any of the methods described above. As shown in cross-section in FIGS. 7A-7D, the microcell walls 735 extend upward from the backing layer 773 and first electrode layer 720 to form the open cells. In an embodiment, a first electrode layer 720 is formed on or at the backing layer 773. While FIGS. 7A-7D show the first electrode layer 720 is continuous and running above the backing layer 773, it is also possible that the first electrode layer 720 is continuous and running below or within the backing layer 773 or it is interrupted by the microcell walls 735. Prior to filling, the microcell array 700 may be cleaned and sterilized to assure that the benefit agents are not compromised prior to use.

The microcells are next filled with a liquid mixture comprising reverse micelles 745 in the hydrophobic liquid 740. As mentioned above, different microcells may include liquid mixtures having different benefit agents or liquid mixtures having different concentrations of the same benefit agent. The hydrophobic liquid may be a biocompatible oil or some other biocompatible hydrophobic liquid. For example, the hydrophobic liquid may comprise a vegetable, fruit, or nut oil.

The microcells may be filled using a variety of techniques. In some embodiments, where a large number of neighboring microcells are to be filled with an identical composition, blade coating may be used to fill the microcells to the depth of the microcell walls 735. In other embodiments, where a variety of different composition are to be filled in a variety of nearby microcell, inkjet-type microinjection can be used to fill the microcells. In yet other embodiment, microneedle arrays may be used to fill an array of microcells with the appropriate liquid mixture(s). The filling may be done in a one-step or multistep process. For example, all of the cells may be partially filled with an amount of liquid mixture. The partially filled microcells are then filled with a liquid mixture that comprises the benefit agent(s) to be delivered.

Figure 7A:
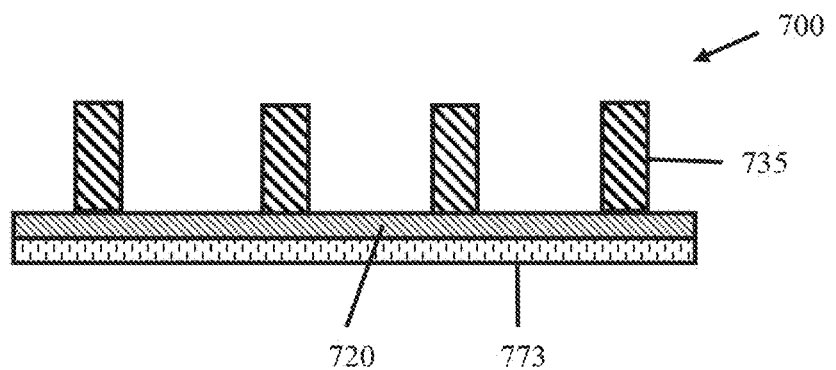
FIGS. 7A-7D illustrate the steps of filling and sealing an array of microcells to be used in a benefit agent delivery system.
Figure 7B:
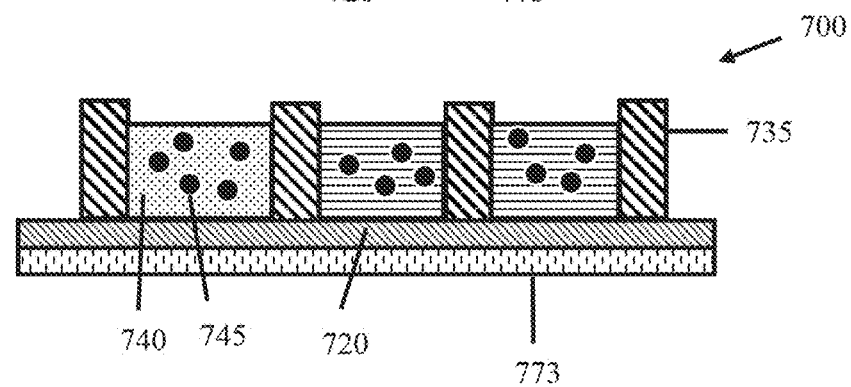
Figure 7C:
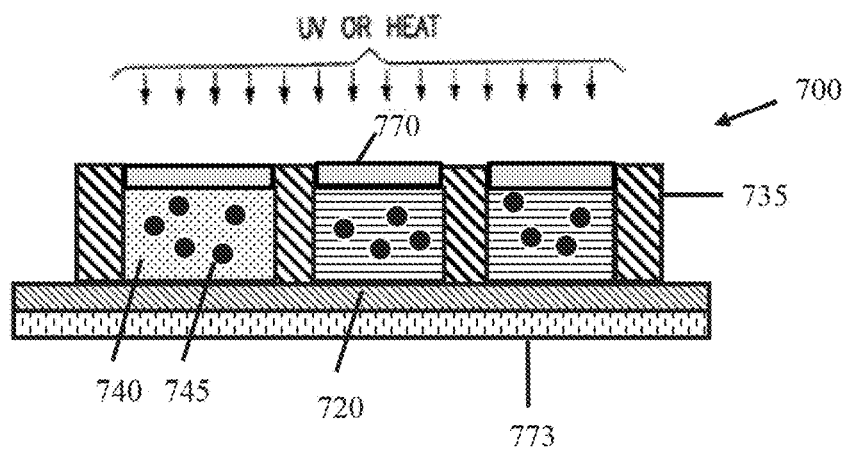
Figure 7D:
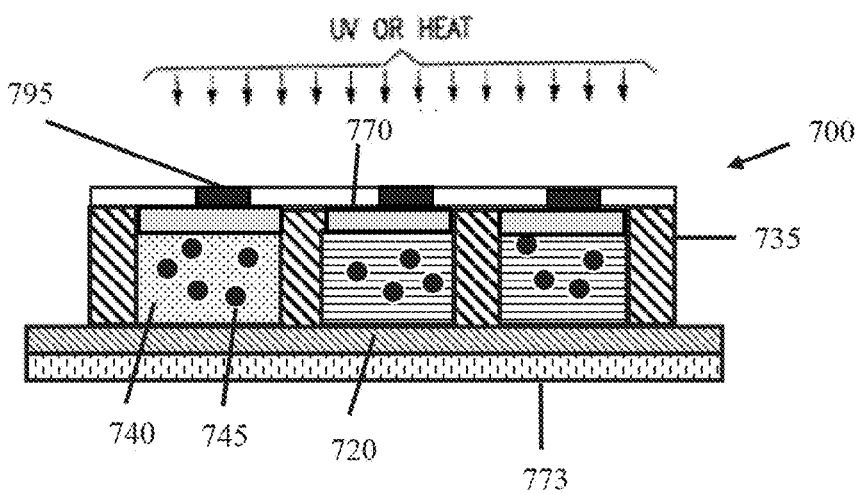

As shown in FIG. 7C, after filling, the layer that spans the openings of the microcells 770 is applied. This may be a porous second electrode layer or a sealing layer. It may comprise a continuous layer or a discontinuous layer (as shown in FIG. 7C). A polymer composition may be used to form layer 770. In some embodiments, the microcell covering/sealing process may involve exposure to heat, dry hot air, or UV radiation. In most embodiments, the polymer should be insoluble or have low solubility with the liquid mixture that is included in the microcells. The polymer composition, which is used to form layer 770, can also be biocompatible and selected to adhere to the sides or tops of the microcell walls 735. An adhesive can also be used to attach the electrode layer onto layer 770. The adhesive may also be electrically conductive. A suitable biocompatible adhesive for sealing layer is a phenethylamine mixture, such as described in U.S. patent application Ser. No. 15/336,841, filed Oct. 30, 2016 and titled "Method for Sealing Microcell Containers with Phenethylamine Mixtures," which is incorporated herein by reference in its entirety. Accordingly, the final microcell structure is mostly impervious to leaks and able to withstand flexing without delamination or separation of the porous second electrode layer, or the sealing layer, if a sealing layer is present In alternate embodiments, a variety of individual microcells may be filled with the desired liquid mixture by using iterative photolithography. The process typically includes coating an array of empty microcells with a layer of positively working photoresist, selectively opening a certain number of the microcells by image-wise exposing the positive photoresist, followed by developing the photoresist, filling the opened microcells with the desired liquid mixture, and covering the opening of the filled microcells. These steps may be repeated to create covered microcells filled with other liquid mixtures. This procedure allows for the formation of large sheets of microcells having the desired ratio of liquid mixtures or concentrations.

In embodiments that the benefit agent delivery system comprises a sealing layer, after the microcells 700 are filled and sealed, the sealed microcell array may be laminated with the porous second electrode layer comprising a plurality of electrodes 795. An adhesive layer may be applied adjacent to the porous second electrode layer, which may be a pressure sensitive adhesive, a hot melt adhesive, or a heat, moisture, or radiation curable adhesive. The laminate adhesive may be post-cured by radiation such as UV through the first electrode layer if the latter is transparent to the radiation. In other embodiments, the porous second electrode layer comprising the plurality of electrodes 795 may be bonded directly to the sealed array of the microcell. In some embodiments, a biocompatible adhesive is then laminated to the assembly. The biocompatible adhesive will allow benefit agents to pass through while keeping the device mobile on a user. Suitable biocompatible adhesives are available from 3M (Minneapolis, MN).

Once the delivery system has been constructed, it may be covered with a release sheet to provide protection. The release sheet may also include adhesives. The benefit agent delivery system may be flexible. This means that it can be folded to a certain extend without breaking, a property similar to a thin rubber sheet. The benefit agent delivery system can be an autonomous system, which that can be easily transported in a small space, such as a handbag, and only needs electric power, which can be a small battery to operate.

Figure 8:
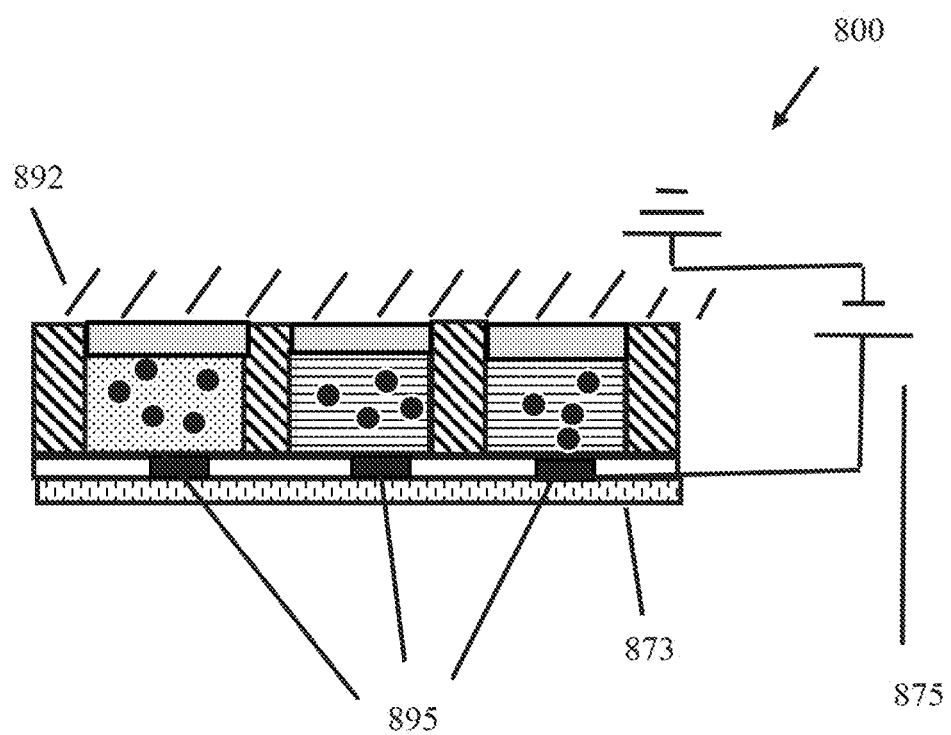
FIG. 8 illustrates an example of a benefit agent delivery system comprising a plurality of microcells, wherein the benefit agent delivery system can be activated by applied an electric field; the microcell may be activated by an electrode while the conductivity of the skin (or other conductive substrate) provides a grounding electrode.

In some embodiments, it will not be necessary to provide a benefit agent delivery system comprising two electrode layers on the opposite sides of the system. For instance, as shown in FIG. 8, the benefit agent delivery system 800 may include a voltage source 875 that is grounded into the surface to which the delivery system is attached 892. This may be especially useful for transdermal delivery of drugs, where the skin's natural conductance is sufficient to provide a ground potential. Application of an electric field to at least one of the electrodes 895, as shown in FIG. 8, may activate the corresponding microcell and trigger the release of the active agent through the porous electrode (or increase the rate of release through the porous electrode). It is appreciated that the porous electrode layer comprises a plurality of electrodes whereby each of the plurality of electrodes can be addressed individually, e.g., with row-column drivers as in an electro-optic display.

Figure 9:
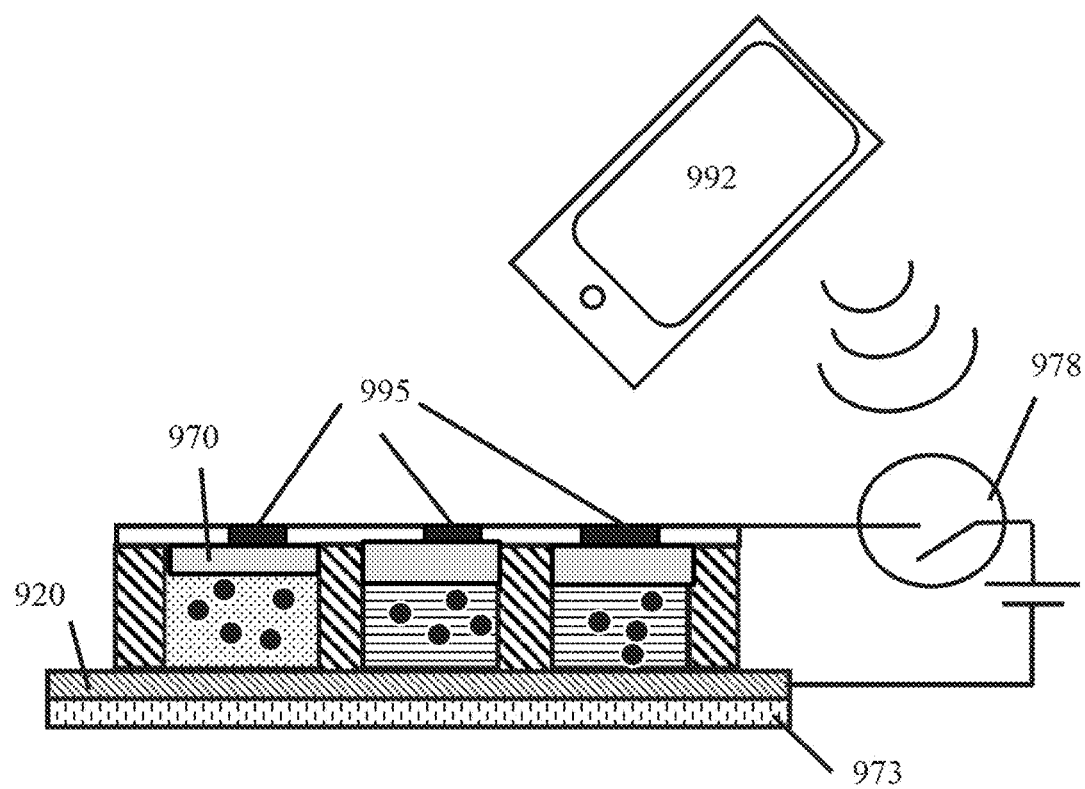
FIG. 9 illustrates an example of a benefit agent delivery system including a plurality of microcells; a switch is coupled to a wireless receiver allowing a user to activate a microcell to trigger the delivery of the benefit agent with an application on a mobile phone or other wireless device.
Figure 10:
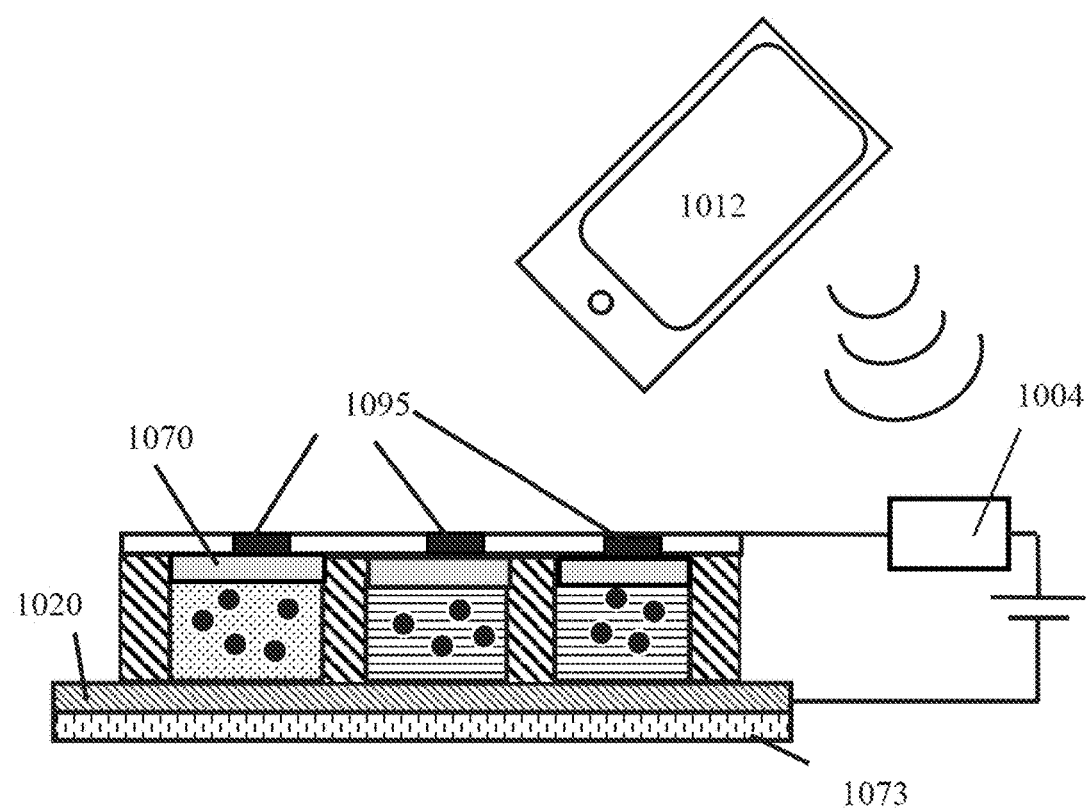
FIG. 10 illustrates an example of a benefit agent delivery system comprising a plurality of microcells; the plurality of electrodes is coupled to a matrix driver that is coupled to a wireless receiver, thereby allowing an application to activate the delivery of the desired benefit agent.

Advanced embodiments of a benefit agent delivery system will include circuitry to allow the benefit agent delivery system to be activated wirelessly with a secondary device 992, such as a smart phone or smart watch. As shown in FIG. 9, a simple system will allow a user to activate electronic/digital switch, which will cause an electric field to open an electronic/digital switch 978, causing an electric field to activate the corresponding microcells, delivering the benefit agent at a desired surface or space (or increasing the rate of release of the benefit agent). In another embodiment, i.e., as shown in FIG. 10, the benefit agent delivery system includes a controller 1004 that independently controls the plurality of electrodes of the electrode layer. Controller 104 may also be able to receive wireless signals from a secondary device 1012. The embodiment of FIG. 10 will allow a user to control, for example, the type of benefit agent that is delivered and the amount at the desired time. Using an application on the secondary device 1012 it may be possible to program the benefit agent delivery system to modify the amount of benefit agent based upon the time of day. In other embodiments, the application may be operatively connected to biometric sensors, e.g., a fitness tracker, whereby the application causes the dosage to be turned off if, e.g., the pulse rate of the user exceeds a preset threshold.

When driving the benefit agent delivery systems of FIGS. 9 and 10, NFC, Bluetooth, WIFI, or other wireless communication function is turned on, allowing a user to manipulate the applied voltage across the microcells in order to activate the desired microcells. The activation can be initiated before or after the benefit agent delivery system is applied on the desired surface or location. In addition, benefit agent release adjustment can be achieved at any time when necessary. Because the microcell activation is controlled by smart watch or smart phone, the percentage and area for all of the microcells at different activation status is known, which means all of the usage data will be available to a user or a provider, including the time of the system activation and the amount of the benefit agent(s) administered. Thus, the system may provide a precise control to the user or another person (i.e. a doctor or health provider) to adjust the benefit agent delivery. Because every microcell can be activated independently, the system is programmable. That is, the overall benefit agent delivery can be programmed by activating each of the plurality of microcells when desired. For a benefit agent delivery system, which is designed to deliver benefit agents transdermally, the skin irritation can be mitigated, because the benefit agent can be released over a period of time. Additionally, in drug delivery applications, patient compliance can be done effectively, because the smart device, which is used to activate the system, can remotely communicate with the physician for data sharing.

Figure 11:
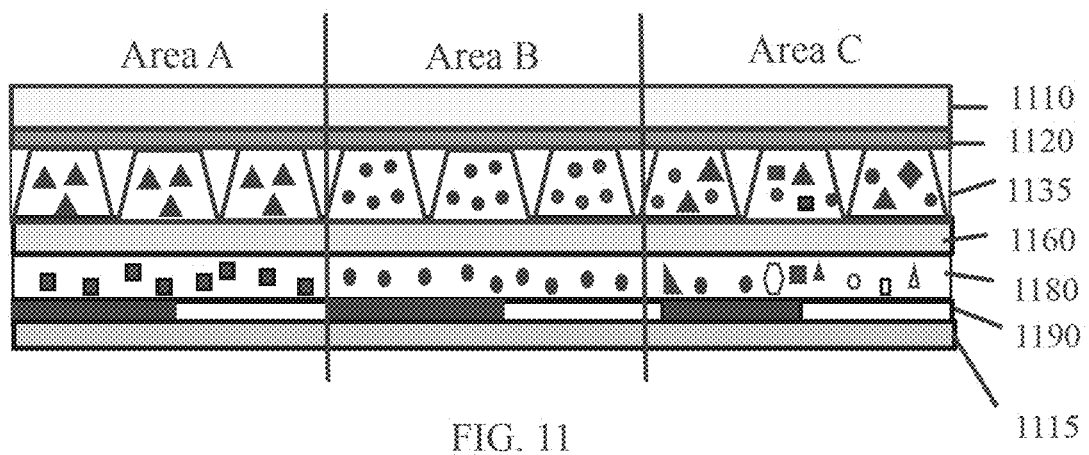
FIGS. 11 and 12 illustrate an example of a benefit agent delivery system wherein the benefit agents are not only loaded into the microcells, but also in other layers, such as an adhesive layer and/or a benefit agent loading layer; different combinations of benefit agents can be included in different areas of the delivery system.

It is to be understood that the invention is not limited to combinations of benefit agents in the microcell, as different benefit agents can be delivered by adding those benefit agents to additional layers of the benefit agent delivery system. FIG. 11 exemplifies a benefit agent delivery system that comprises in order, a backing layer 1110, a first electrode layer 1120, a microcell layer 1135, a sealing layer 1160, an adhesive layer 1180, a porous second electrode layer 1190, and a release sheet 1115. As shown in FIG. 11, the benefit agents may be present in, for example, the adhesive layer 1180.

Area A of FIG. 11 exemplified two different benefit agents being loaded into the microcell layer 1135 and the adhesive layer 1180. In some embodiments, the two benefit agents may be delivered at the same time. They may also have different delivery profiles. The system also provides a way to deliver different benefit agents with different physical properties, such as different hydrophobicities. For example, a hydrophilic benefit agent can be loaded into the plurality of microcells at high loading. In this embodiment, the adhesive layer may include a hydrophobic benefit agent. Accordingly, the release profile of the two benefit agents can also be adjusted nearly independently. This system overcomes the problem of stabilizing a benefit agent with unfavorable solubility with, e.g., surfactants, capsules, etc.

Area B of FIG. 11 illustrates an embodiment in which the same benefit agent is loaded in both the microcells and the adhesive layer 1180. Depending on the characteristics of the benefit agent, this method can help to load larger quantities of benefit agent into the benefit agent delivery system, which can help to increase the benefit agent release amount and control the release profile.

Area C of FIG. 11 illustrates an embodiment in which a combination of benefit agents is loaded either into the microcell, or into the adhesive layer 1180, or into both layers. The benefit agents in the microcell composition and adhesive layer can be the same or different. The number of benefit agents in the microcell formulation and the number of benefit agents in the adhesive layer can also be the same or different.

Figure 12:
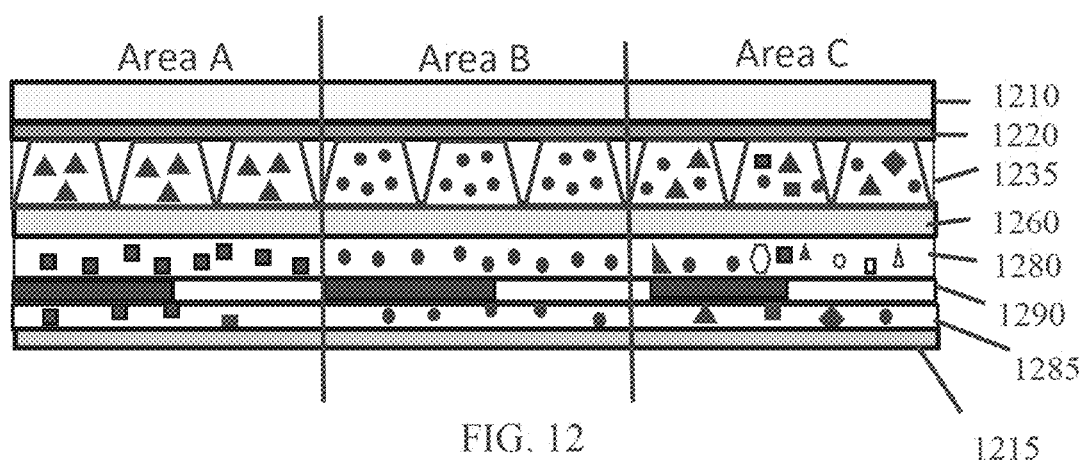

A benefit agent-loading layer 1285 can be also included into the benefit agent delivery system adjacent to the release sheet 1215, as shown in FIG. 12. The amount and types of benefit agents in the benefit agent-loading layer 1285 can be independent of the loading in the microcells and/or in the adhesive layer. The benefit agent can be introduced into only some portions of the adhesive layer, or it can present in both adhesive 1280 and the benefit agent-loading layer 1285. The benefit agent-loading layer 1285 may be porous. In another example, the benefit-loading layer may be located between the sealing layer 1260 and the adhesive layer 1280.

The benefit agent delivery system may also comprise a porous diffusion layer or a rate control layer that is disposed between the sealing layer and the electrode layer. If there is an adhesive layer adjacent to the sealing layer, the porous diffusion layer or the rate control layer may be disposed between the adhesive layer and the electrode layer. The porous diffusion layer or the rate control layer and the adhesive layer may be integrated into one layer, which may have volume resistivity of less than $10^{-10}$ Ohm*cm, or less than $10^{-9}$ Ohm*cm. That is, the porous diffusion layer or the rate control layer may also serve as an adhesive layer, establishing an adhesive connection between the sealing layer and the electrode layer. The porous diffusion layer or the rate control layer and the electrode layer may also be integrated into one layer.

The porous diffusion layer may have average pore size larger than 0.2 nm. The rate control layer may have average pore size of 0.2 nm and smaller. The porous diffusion layer and the rate control layer may control the rate of release of the benefit agent by its porosity, pore size, layer thickness, the chemical structure, and the polarity of the material from which it is constructed. Thus, for example, a rate control layer, positioned adjacent to the sealing layer or adjacent to the electrode layer, and made with a nonpolar polymer such as polyethylene having some porosity level may reduce the rate of release of relatively polar benefit agents, such as, for example benefit agents that are soluble or dispersible in water. In addition, a rate control layer having low porosity or higher thickness may slow down the delivery of benefit agents.

As mentioned above, various layers of the benefit agent delivery system may be combined or integrated in a single layer. For example, an adhesive layer an adjacent porous second electrode layer may also be integrated into one layer. The same may be true for the combination of the porous diffusion layer or the rate control layer and the porous second electrode layer, the combination of the sealing layer and the benefit agent-loading layer, the combination of the benefit agent-loading layer and the rate control layer, etc.

The benefit agent delivery system of the present invention may be operated by a method comprising the steps of:
(1) Providing a benefit agent delivery system comprising
  (a) a first electrode layer, (b) a microcell layer comprising a plurality of microcells, wherein each microcell includes an opening, and wherein each microcell contains a liquid mixture, wherein the liquid mixture comprises reverse micelles in a hydrophobic liquid that are formed from a polar liquid, an anionic or cationic surfactant, and a benefit agent, (d) a porous second electrode layer spanning the opening of each microcell, and (e) a voltage source that is coupled to the first electrode layer and the porous second electrode layer; wherein the first electrode layer, the microcell layer, and the porous second electrode layer are vertically stacked upon each other;
(2) Applying a first voltage on a microcell via the voltage source that causes the migration of the reverse micelles of the microcell towards the porous second electrode, increases the rate of release of the benefit agent through the porous second electrode layer compared to the rate of release of the benefit agent through the porous second electrode layer when no voltage is applied;

(3) Applying a second voltage on a microcell via the voltage source, the second voltage having polarity opposite to the polarity of the first voltage, that causes the migration of the reverse micelles of the microcell away from the porous second electrode and reduces the rate of release of the benefit agent through the porous second electrode layer compared to the rate of release of the benefit agent through the porous second electrode layer when no voltage is applied.

The rate of release of the benefit agent of a microcell of the benefit agent delivery system may be increased or decreased depending on the polarity of the electric field applied across the microcell compared to rate of release of the benefit agent from the microcell without application of an electric field. Furthermore, the rate of increase or decrease can be controlled by the amplitude of the voltage and the period of time that the voltage is applied. For example, in the case of reverse micelles stabilized by an anionic surfactant, wherein application of a first voltage makes the porous second electrode layer at a microcell positive, the higher the amplitude of the applied first voltage, the higher is the increase in the rate of release of the benefit agent of the microcell. Analogously, the longer the first voltage is applied across the microcell, the higher is the increase in the rate of release of the benefit agent of the microcell. In the case of reverse micelles stabilized by an anionic surfactant, wherein application of a second voltage makes the porous second electrode layer at a microcell negative, the higher the amplitude of the applied second voltage, the higher is the decrease of the rate of release of the benefit agent of the microcell. Also, the longer the second voltage is applied across the microcell, the higher is the decrease of the rate of release of the benefit agent of the microcell.

The electric field of the method of operating a benefit agent delivery system (first voltage and second voltage) may be applied for more than 1 s, or for more than 5 s, or more than 10 s, or more than 20 s, or for more than 50 s, or for more than 100 s, or for more than 200 s, or for more than 500 s, or for more than 1000 s, or for more than 10,000 s. The electric field of the method of operating a benefit agent delivery system may be applied from 1 s to 1000 s, or from 2 s to 800 s, or from 5 s to 700 s, or from 10 s to 600 s, or from 30 s to 500 s, or from 60 s to 400 s, or from 100 s to 1000 s.

The applied field (first voltage and second voltage) may be applied via a voltage source that is coupled to the first electrode layer and the porous second electrode layer. The electric field may be an alternating electric field. The first voltage and the second voltage of the applied alternating field may be from 0.5 V to 250 V, or from 1 V to 220 V, or to 5 V to 200 V, or from 10 V to 180 V, or from 20 V to 150 V, or from 50 V to 120 V. The first voltage and the second voltage of the applied alternating field may be higher than 0.5 V, or higher than 1 V, or higher than 5 V, or higher than 10 V, or higher than 20 V, or higher than 50 V, or higher than 100 V, or higher than 150 V, or higher than 200 V, or higher than 220 V. The frequency of the alternating electric field may be from 4 Hz to 1000 Hz, or from 5 Hz to 800 Hz, or from 10 Hz to 600 Hz, or from 20 Hz to 500 Hz, or from 50 Hz to 300 Hz, or from 100 Hz to 250 Hz. The frequency of the alternating electric field may be higher than 5 Hz, or higher than 10 z, or higher than 20 Hz, or higher than 50 Hz, or higher than 100 Hz, or higher than 200 Hz, or higher than 300 Hz, or higher than 500 Hz.

The electric field (first voltage and second voltage) may be a direct electric field. The first voltage and second voltage of the applied direct field may be from 1 V to 250 V, or to 5 V to 200 V, or from 10 V to 180 V, or from 20 V to 150 V, or from 50 V to 120 V. The first voltage and second voltage of the applied alternating field may be higher than 0.5 V, or higher than 1 V, or higher than 5 V, or higher than 10 V, or higher than 20 V, or higher than 50 V, or higher than 100 V, or higher than 150 V, or higher than 200 V, or higher than 220 V.

The method of operating a benefit agent delivery system may further comprise a step of controlling the rate of release of the benefit agent through the porous second electrode by the selection of the applied voltage potential.

As disclosed before, each microcell of the plurality of microcells can be independently activated on demand. Thus, the system has the flexibility of delivering variable quantities of benefit agents at different times. Additionally, the microcell arrays may be loaded with different benefit agents, thereby providing a mechanism to deliver different or complimentary benefit agents on demand.

In addition to more conventional applications, such as transdermal delivery of pharmaceutical compounds, the benefit agent delivery system may be the basis for delivering agricultural nutrients. The microcell arrays can be fabricated in large sheets that can be used in conjunction with hydroponic growing systems, or they can be integrated into hydrogel film farming, such as demonstrated by Mebiol, Inc. (Kanagawa, Japan). The benefit agent delivery system can be incorporated into the structural walls of smart packing, as well. The delivery system, for example, makes it possible to have long-term release of antioxidants into a package containing fresh vegetables or other items. Such packaging could dramatically improve the shelf life of certain foods and other items yet will only require the amount of antioxidant necessary to maintain freshness until the package is opened.

Figure 13:
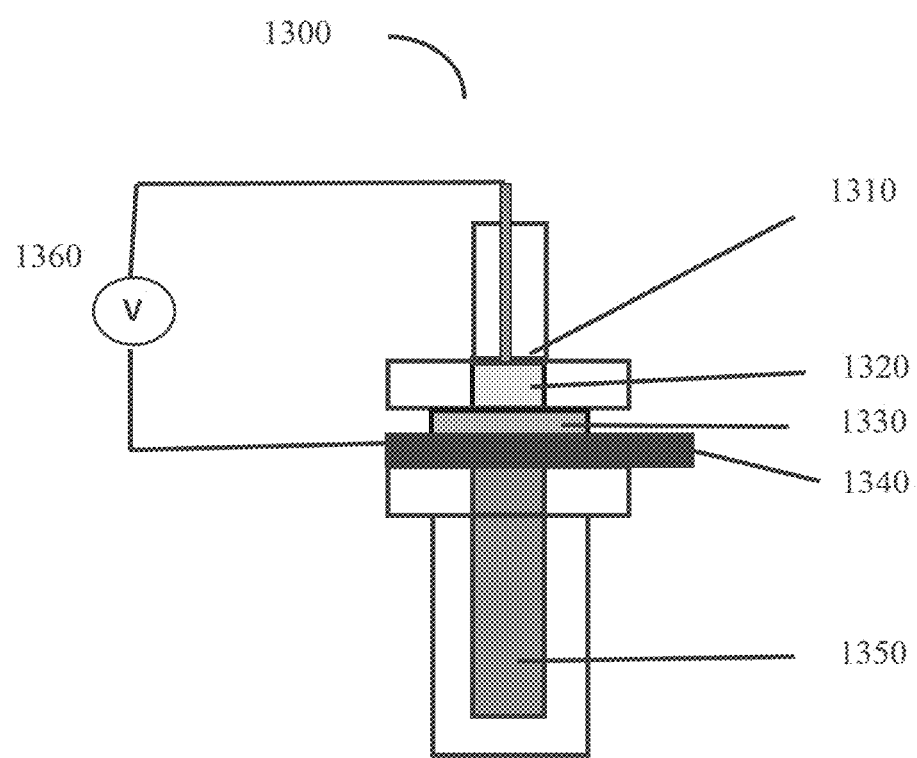
FIG. 13 illustrates the Franz cell set up that may be used for the evaluation of the effectiveness of the benefit agent delivery system.

The effect of the application of an electrical field on the rate of release of a water soluble benefit agent via a porous substrate may be determined using a Franz cell as shown in FIG. 13. Specifically, a Franz cell 1300 may be set-up comprising a first electrode 1310 made from copper wire, a donor solution compartment 1320 (containing reverse micelles in a hydrophobic liquid), a dialysis membrane 1330, a porous metal electrode 1340, and a receptor solution 1350, as shown in FIG. 13. The two electrodes are coupled by a voltage source 1360. The porous electrode dialysis membrane 1330 and the porous metal electrode 1340 are placed between the donor solution compartment 1320 and the receptor solution compartment 1350. A formulation comprising reverse micelles (comprising a benefit agent in water or another polar liquid and an anionic surfactant) in hydrophobic liquid is added into the donor compartment 1320 of Franz cell. The copper wire electrode 1310 may be suspended in the liquid mixture of the donor compartment 1320. The electrodes are connected to a voltage source 1360. The electric field is provided by a function generator and amplifier at 25 V and 50 Hz for a duration of 60 seconds. A sample of the receptor liquid can be extracted at various times after the application of the electric field. The extracted samples can be then analyzed using a chromatographic technique to determine the content of the benefit agent in the receptor liquid.

Thus, the invention provides for a benefit agent delivery system including a plurality of microcells, which include a liquid mixture, wherein the liquid mixture comprises a benefit agent, and a sealing layer comprising a metallic material in a polymer. Application of a voltage on the system results in the migration of the metallic material of the sealing and the creation of a porous sealing layer. The porosity of the sealing layer permits for the benefit agent to be delivered from the benefit agent delivery system. This disclosure is not limiting, and other modifications to the invention, not described, but self-evident to one of skill in the art, are to be included in the scope of the invention.

While various embodiments of the invention have been shown and described herein, it will be understood that such embodiments are provided by way of example only. Numerous variations, changes, and substitutions will occur to those skilled in the art without departing from the spirit of the invention. Accordingly, it is intended that the appended claims cover all such variations as fall within the spirit and scope of the invention.

The invention claimed is:

1. A benefit agent delivery system comprising:
a first electrode layer;
a microcell layer comprising a plurality of microcells, each microcell including a first opening, and each microcell containing a liquid mixture;
a porous second electrode layer spanning the first opening of each microcell; and
the first electrode layer, the microcell layer, and the porous second electrode layer being vertically stacked upon each other;
the liquid mixture comprising reverse micelles in a hydrophobic liquid that are formed from a polar liquid, a surfactant, and a benefit agent, the surfactant being an anionic surfactant or a cationic surfactant; and
wherein application of a first voltage across a microcell via the first electrode layer and the porous second electrode layer having polarity that causes the migration of the reverse micelles in the microcell towards the porous second electrode increases the rate of release of the benefit agent through the porous second electrode layer compared to the rate of release of the benefit agent through the porous second electrode layer when no voltage is applied, and
wherein application of a second voltage across a microcell via the first and second electrode layers, the second voltage having polarity opposite to the polarity of the first voltage, causes the migration of the reverse micelles in the microcell away from the porous second electrode layer and reduces the rate of release of the benefit agent through the porous second electrode layer compared to the rate of release of the benefit agent through the porous second electrode layer when no voltage is applied.

2. The benefit agent delivery system of claim 1, wherein the reverse micelle has an average diameter of from 10 nm to 10 µm.

3. The benefit agent delivery system of claim 1, wherein each microcell further includes a second opening, wherein the second opening is opposite side from the first opening of the microcell, and wherein the first electrode layer spans the second opening of each microcell.

4. The benefit agent delivery system of claim 1, further comprising a sealing layer, wherein the sealing layer is disposed between the microcell layer and the porous second electrode layer.

5. The benefit agent delivery system of claim 1, further comprising a voltage source that is coupled to the first electrode layer and the porous second electrode layer.

6. The benefit agent delivery system of claim 1, wherein the electric field is alternating.

7. The benefit agent delivery system of claim 6, wherein the alternating electric field has voltage of from 1 V to 250 V and frequency of from 5 Hz to 1000 Hz.

8. The benefit agent delivery system of claim 1, wherein the electric field is direct (DC), and wherein the voltage of the applied electric field is from 1 V to 250 V.

9. The benefit agent delivery system of claim 1, wherein at least one of the first electrode layer and the porous second electrode layer comprises an active matrix of individual electrodes whereby said individual electrodes can be addressed individually.

10. The benefit agent delivery system of claim 1, wherein the surfactant is a polyester having a quaternary ammonium functional group.

11. The benefit agent delivery system of claim 1, wherein the reverse micelles of the liquid mixture further comprise stabilizing particles.

12. The benefit agent delivery system of claim 1, wherein the average pore size of the porous second electrode layer is larger than 100 nm.

13. The benefit agent delivery system of claim 4, wherein the sealing layer further comprises a conductive material selected from the group consisting of carbon black, carbon nanotubes, graphene, a dopant, and a conductive polymer.

14. The benefit agent delivery system of claim 1, wherein each of the plurality of microcells contains a benefit agent selected from the group consisting of a pharmaceutical agent, a vaccine, an antibody, a hormone, a protein, a nucleic acid, a nutraceutical agent, a nutrient, a cosmetic agent, a fragrance, a malodor removing agent, an agricultural agent, an air care agent, an anti-microbial agent, and a preservative.

15. The benefit agent delivery system of claim 4, wherein the sealing layer and the porous electrode layer are integrated into one layer.

16. The benefit agent delivery system of claim 4, further comprising a porous diffusion layer or a rate control layer, which is located adjacent to the porous second electrode layer, wherein the porous second electrode layer is disposed between the sealing layer and the porous diffusion layer or the rate control layer.

17. The benefit agent delivery system of claim 4, further comprising a first adhesive layer disposed between the sealing layer and the porous second electrode layer.

18. The benefit agent delivery system of claim 4, further comprising a release sheet adjacent to the porous second electrode layer, wherein the porous second electrode layer is disposed between the sealing layer and the release sheet.

19. The benefit agent delivery system of claim 17, further comprising a second adhesive layer, wherein the second adhesive layer is disposed between the porous second electrode layer and the release sheet.

20. A method for operating a benefit agent delivery system comprising the steps of:
providing a benefit agent delivery system comprising (a) a first electrode layer, (b) a microcell layer comprising a plurality of microcells, each microcell including an opening, and each microcell containing a liquid mixture, the liquid mixture comprising reverse micelles in a hydrophobic liquid that are formed from a polar liquid, an anionic or cationic surfactant, and a benefit agent, (d) a porous second electrode layer spanning the opening of each microcell, and (e) a voltage source that is coupled to the first electrode layer and the porous second electrode layer; wherein the first electrode layer, the microcell layer, and the porous second electrode layer are vertically stacked upon each other;

applying a first voltage on a microcell via the voltage source that causes the migration of the reverse micelles of the microcell towards the porous second electrode, increasing the rate of release of the benefit agent through the porous second electrode layer compared to the rate of release of the benefit agent through the porous second electrode layer when no voltage is applied; and applying a second voltage on a microcell via the voltage source, the second voltage having polarity opposite to the polarity of the first voltage, that causes the migration of the reverse micelles of the microcell away from the porous second electrode, reducing the rate of release of the benefit agent through the porous second electrode layer compared to the rate of release of the benefit agent through the porous second electrode layer when no voltage is applied.

\* \* \* \* \*